US008870964B2

(12) United States Patent
Lipman et al.

(10) Patent No.: US 8,870,964 B2
(45) Date of Patent: *Oct. 28, 2014

(54) PROSTHETIC CONDYLAR JOINTS WITH ARTICULATING BEARING SURFACES HAVING A TRANSLATING CONTACT POINT DURING ROTATION THEREOF

(75) Inventors: Joseph D. Lipman, New York, NY (US); Donald L. Bartel, Ithaca, NY (US); Timothy M. Wright, New York, NY (US)

(73) Assignee: New York Society for the Ruptured and Crippled Maintaining the Hospital for Special Surgery, New York, NY (US)

( * ) Notice: Subject to any disclaimer, the term of this patent is extended or adjusted under 35 U.S.C. 154(b) by 7 days.

This patent is subject to a terminal disclaimer.

(21) Appl. No.: 12/947,572

(22) Filed: Nov. 16, 2010

(65) Prior Publication Data
US 2011/0125275 A1 May 26, 2011

Related U.S. Application Data

(60) Provisional application No. 61/281,362, filed on Nov. 16, 2009, provisional application No. 61/261,575, filed on Nov. 16, 2009.

(51) Int. Cl.
*A61F 2/38* (2006.01)
*A61F 2/42* (2006.01)
(52) U.S. Cl.
CPC ............. *A61F 2/3886* (2013.01); *A61F 2/3804* (2013.01); *A61F 2/4202* (2013.01)
USPC .................................................... 623/20.27

(58) Field of Classification Search
USPC ...................... 623/20.14, 20.15, 20.25–20.36
See application file for complete search history.

(56) References Cited

U.S. PATENT DOCUMENTS 3,748,662 A * 7/1973 Helfet ........................ 623/20.31
4,209,861 A * 7/1980 Walker et al. .............. 623/20.27

(Continued)

FOREIGN PATENT DOCUMENTS

| EP | 1 132 063 | 9/2001 |
| EP | 1 174 099 | 1/2002 |
| WO | WO 96-23460 | 8/1996 |

OTHER PUBLICATIONS

"Discovery Elbow System, Surgical Technique" Biomet Orthopedics, 2008.

*Primary Examiner* — Alvin Stewart
(74) *Attorney, Agent, or Firm* — Leason Ellis LLP

(57) ABSTRACT

A prosthetic joint according to the present invention includes a first implant component for attachment to a first bone and a second implant component for attachment to a second bone. The first implant component has a condylar portion that includes first and second condylar bearing surfaces and similarly, the second implant component has bearing surfaces that receive and are complementary to the first and second condylar bearing surfaces. Each of the first and second condylar bearing surfaces and each of the bearing surfaces of the second implant component has a cross-section in a coronal plane that exhibits two different radii and a contact point is established between the first and second condylar bearing surfaces and the bearing surfaces of the second implant component. The bearing surfaces of the respective implant components are configured such that varus and valgus rotation of the first implant component relative to the second implant component causes the contact point to move outwardly.

11 Claims, 29 Drawing Sheets

(56) References Cited

U.S. PATENT DOCUMENTS

| | | | | |
|---|---|---|---|---|
| 4,309,778 | A * | 1/1982 | Buechel et al. | 623/20.29 |
| 5,007,933 | A * | 4/1991 | Sidebotham et al. | 623/20.27 |
| 5,116,375 | A * | 5/1992 | Hofmann | 623/20.27 |
| 5,133,758 | A * | 7/1992 | Hollister | 623/20.31 |
| 5,147,405 | A * | 9/1992 | Van Zile et al. | 623/20.27 |
| 5,282,870 | A * | 2/1994 | Moser et al. | 623/20.31 |
| 5,326,361 | A * | 7/1994 | Hollister | 623/20.31 |
| 5,330,534 | A * | 7/1994 | Herrington et al. | 623/20.27 |
| 5,370,699 | A * | 12/1994 | Hood et al. | 623/20.28 |
| 5,549,686 | A * | 8/1996 | Johnson et al. | 623/20.27 |
| 5,609,643 | A * | 3/1997 | Colleran et al. | 623/20.29 |
| 5,782,921 | A * | 7/1998 | Colleran et al. | 623/20.15 |
| 5,824,100 | A * | 10/1998 | Kester et al. | 623/20.31 |
| 5,871,539 | A * | 2/1999 | Pappas | 623/20.31 |
| 5,871,546 | A * | 2/1999 | Colleran et al. | 623/20.28 |
| 5,935,173 | A * | 8/1999 | Roger et al. | 623/20.31 |
| 6,027,534 | A | 2/2000 | Wack et al. | |
| 6,039,764 | A | 3/2000 | Pottenger et al. | |
| 6,152,960 | A * | 11/2000 | Pappas | 623/20.31 |
| 6,165,223 | A * | 12/2000 | Metzger et al. | 623/20.27 |
| 6,168,629 | B1 * | 1/2001 | Timoteo | 623/20.27 |
| 6,203,576 | B1 * | 3/2001 | Afriat et al. | 623/20.27 |
| 6,206,926 | B1 * | 3/2001 | Pappas | 623/20.27 |
| 6,235,060 | B1 * | 5/2001 | Kubein-Meesenburg et al. | 623/20.31 |
| 6,379,387 | B1 | 4/2002 | Tornier | |
| 6,406,497 | B2 * | 6/2002 | Takei | 623/20.31 |
| 6,413,279 | B1 * | 7/2002 | Metzger et al. | 623/20.29 |
| 6,416,552 | B1 * | 7/2002 | Hoeppner et al. | 623/20.15 |
| 6,443,991 | B1 * | 9/2002 | Running | 623/20.27 |
| 6,458,160 | B2 * | 10/2002 | Biegun et al. | 623/20.27 |
| 6,491,726 | B2 * | 12/2002 | Pappas | 623/20.29 |
| 6,558,427 | B2 * | 5/2003 | Leclercq et al. | 623/20.33 |
| 6,699,291 | B1 * | 3/2004 | Augoyard et al. | 623/20.27 |
| 6,726,723 | B2 * | 4/2004 | Running | 623/20.27 |
| 6,730,128 | B2 * | 5/2004 | Burstein | 623/20.27 |
| 6,764,516 | B2 * | 7/2004 | Pappas | 623/20.29 |
| 6,770,097 | B2 * | 8/2004 | Leclercq | 623/20.15 |
| 6,797,005 | B2 * | 9/2004 | Pappas | 623/20.27 |
| 6,890,357 | B2 | 5/2005 | Tornier | |
| 6,902,582 | B2 * | 6/2005 | Kubein-Meesenburg et al. | 623/20.31 |
| 6,972,039 | B2 * | 12/2005 | Metzger et al. | 623/20.29 |
| 7,081,137 | B1 * | 7/2006 | Servidio | 623/20.14 |
| 7,160,330 | B2 * | 1/2007 | Axelson et al. | 623/20.14 |
| 7,247,170 | B2 | 7/2007 | Graham et al. | |
| 7,326,252 | B2 * | 2/2008 | Otto et al. | 623/20.15 |
| 7,413,577 | B1 * | 8/2008 | Servidio | 623/20.14 |
| 7,422,605 | B2 * | 9/2008 | Burstein et al. | 623/20.33 |
| 7,449,028 | B2 | 11/2008 | Ball | |
| 7,678,152 | B2 * | 3/2010 | Suguro et al. | 623/20.27 |
| 7,837,737 | B2 * | 11/2010 | Hedley et al. | 623/20.35 |
| 7,875,081 | B2 * | 1/2011 | Lipman et al. | 623/20.27 |
| 7,896,924 | B1 * | 3/2011 | Servidio | 623/20.3 |
| 7,922,771 | B2 * | 4/2011 | Otto et al. | 623/20.31 |
| 7,938,862 | B2 * | 5/2011 | Naegerl | 623/20.21 |
| 7,981,159 | B2 * | 7/2011 | Williams et al. | 623/20.21 |
| 8,075,626 | B2 * | 12/2011 | Dun | 623/20.27 |
| 2001/0034555 | A1 * | 10/2001 | Pappas | 623/20.29 |
| 2002/0010512 | A1 * | 1/2002 | Takei | 623/20.31 |
| 2003/0004577 | A1 * | 1/2003 | Running | 623/20.27 |
| 2003/0009232 | A1 * | 1/2003 | Metzger et al. | 623/20.29 |
| 2004/0122522 | A1 | 6/2004 | Kubein-Meesenburg et al. | 623/20.31 |
| 2004/0143339 | A1 * | 7/2004 | Axelson et al. | 623/20.21 |
| 2005/0055102 | A1 * | 3/2005 | Tornier et al. | 623/20.32 |
| 2007/0162143 | A1 * | 7/2007 | Wasielewski | 623/20.14 |
| 2007/0239281 | A1 * | 10/2007 | Gotte et al. | 623/20.27 |
| 2008/0097615 | A1 * | 4/2008 | Lipman et al. | 623/20.27 |
| 2009/0048680 | A1 * | 2/2009 | Naegerl | 623/20.14 |
| 2009/0204221 | A1 * | 8/2009 | Walker | 623/20.27 |
| 2009/0319047 | A1 * | 12/2009 | Walker | 623/20.15 |
| 2009/0326663 | A1 * | 12/2009 | Dun | 623/20.21 |
| 2009/0326666 | A1 * | 12/2009 | Wyss et al. | 623/20.29 |
| 2010/0016979 | A1 * | 1/2010 | Wyss et al. | 623/20.27 |
| 2010/0042224 | A1 * | 2/2010 | Otto et al. | 623/20.27 |
| 2010/0161067 | A1 * | 6/2010 | Saleh et al. | 623/20.31 |
| 2010/0249940 | A1 * | 9/2010 | Sanford | 623/20.27 |
| 2011/0066246 | A1 * | 3/2011 | Ries et al. | 623/20.27 |
| 2011/0118847 | A1 * | 5/2011 | Lipman et al. | 623/20.27 |
| 2011/0125275 | A1 * | 5/2011 | Lipman et al. | 623/20.11 |
| 2011/0125279 | A1 * | 5/2011 | Lipman et al. | 623/20.27 |
| 2011/0125280 | A1 * | 5/2011 | Otto et al. | 623/20.28 |
| 2011/0190897 | A1 * | 8/2011 | Guidera et al. | 623/20.27 |
| 2012/0029649 | A1 * | 2/2012 | Collazo et al. | 623/20.28 |
| 2012/0059483 | A1 * | 3/2012 | Greenhalgh et al. | 623/20.11 |
| 2012/0095564 | A1 * | 4/2012 | Mihalko et al. | 623/20.27 |

* cited by examiner

PROSTHETIC CONDYLAR JOINTS WITH ARTICULATING BEARING SURFACES HAVING A TRANSLATING CONTACT POINT DURING ROTATION THEREOF

CROSS REFERENCE TO RELATED APPLICATION

The present application claims the benefit of U.S. patent application Ser. Nos. 61/281,362, filed Nov. 16, 2009, and 61/261,575, filed Nov. 16, 2009, each of which is hereby incorporated by reference in its entirety.

TECHNICAL FIELD

The present invention relates to prosthetic joints and more particularly, to prosthetic condylar joints for primary and revision surgery that offer improved stability of the joint during rotation (varus/valgus).

BACKGROUND

Joint replacement surgery is quite common and it enables many individuals to function normally when they otherwise would not be possible to do so. Typically, an artificial joint includes metallic, ceramic and/or plastic components that are fixed to existing bone. One type of joint is a condylar or condyloid joint (ellipsoidal joint) in which an ovoid articular surface or condyle is received into an elliptical cavity. A condylar joint is better called bicondylar due to two distinct surfaces on one bone articulating with corresponding distinct surfaces on another bone. There are two male surfaces on one bone and are of the same type (e.g., ovoid).

One of the more common joints that undergoes replacement surgery is the knee. Knee arthroplasty is a well known surgical procedure by which a diseased and/or damaged natural knee joint is replaced with a prosthetic knee joint. Traditionally the joint surfaces associated with implant components are approximated by toroidal or donut shaped surfaces on both the insert and the condylar surfaces of the femoral component which transfer load from the femur to the tibia through an insert component. The total joint, once implanted, is stabilized and controlled in part by these surfaces and in part by the soft tissues surrounding and encapsulating the knee.

Total knee arthroplasty (TKA) devices can fail for reasons such as aseptic loosening, instability, or infection. Failure usually requires revision surgery. Revision implants have been developed that include a post on the polyethylene tibial component that articulates within a recess (intercondylar box) in the femoral component. The objective of this so called constrained condylar knee (CCK) implant is to rely on contact between the box and the post within the joint itself to restrain and limit rotation of the knee (varus/valgus rotations). This constraint is also beneficial in primary TKA if the soft tissues cannot be balanced to achieve an adequately stabilized and controlled joint.

In addition, other joints that have similar condyle structures to the knee, such as the elbow and ankle, etc., likewise suffer from the same limitations and deficiencies described above with reference to the knee. It would thus also be likewise desirable to produce an elbow or ankle replacement with an articular surface designed to gradually shift the contact point outwardly as more varus/valgus motion is initiated, thus increasing the restoring moment at the joint.

Based on the aforementioned, there is a need for prosthetic condylar joints with articulating bearing surfaces having a translating contact point during rotation (varus/valgus) thereof.

SUMMARY

A prosthetic joint according to the present invention includes a first implant component for attachment to a first bone and a second implant component for attachment to a second bone. The first implant component has a condylar portion that includes first and second condylar bearing surfaces and similarly, the second implant component has bearing surfaces that receive and are complementary to the first and second condylar bearing surfaces. Each of the first and second condylar bearing surfaces and each of the bearing surfaces of the second implant component has a cross-section in a coronal plane that exhibits two different radii and a contact point is established between the first and second condylar bearing surfaces and the bearing surfaces of the second implant component. The bearing surfaces of the respective implant components are configured such that varus and valgus rotation of the first implant component relative to the second implant component causes the contact point to move outwardly (laterally toward a lateral edge thereof).

In contrast to conventional implants, the condylar type implants of the present invention includes nontoroidal surface geometry on the joint bearing surfaces to provide improved stability and performance of the joint during rotation (varus/valgus). A medial (inner) radius of each of the first and second condylar bearing surfaces is less than a lateral (outer) radius thereof, with the medial radius and lateral radius being two tangent radii.

In one embodiment, the joint is a knee joint and the first bone is a femur bone and the second bone is a tibia bone. In another embodiment, the joint is an elbow joint and the first bone is a humerus bone and the second bone is an ulna bone. In yet another embodiment, the joint is an ankle joint and the first bone is a tibia bone and the second bone is a talus bone.

These and other aspects, features and advantages shall be apparent from the accompanying Drawings and description of certain embodiments of the invention.

BRIEF DESCRIPTION OF THE DRAWINGS

A few exemplary embodiments of the invention are depicted in the following figures, in which.

DETAILED DESCRIPTION OF EXEMPLARY EMBODIMENTS

Figure 1:
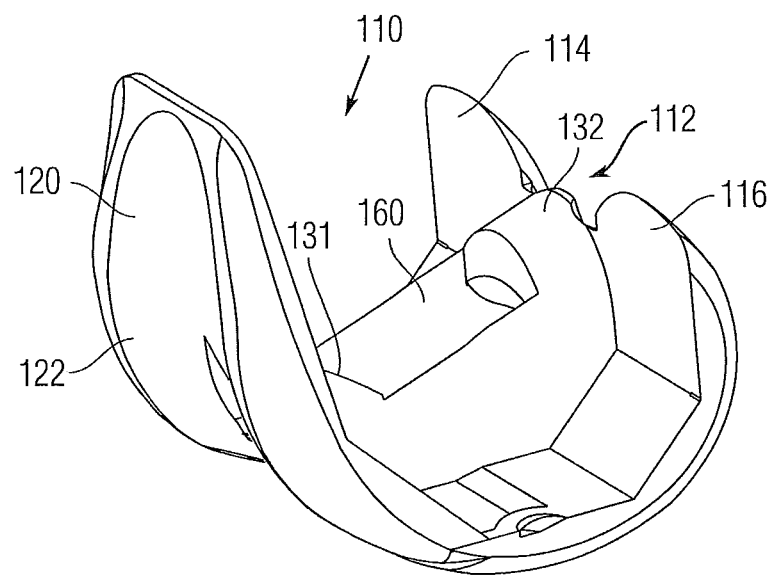
FIG. 1 is side perspective view of a femoral component that forms a part of a knee joint prosthesis.
Figure 2:
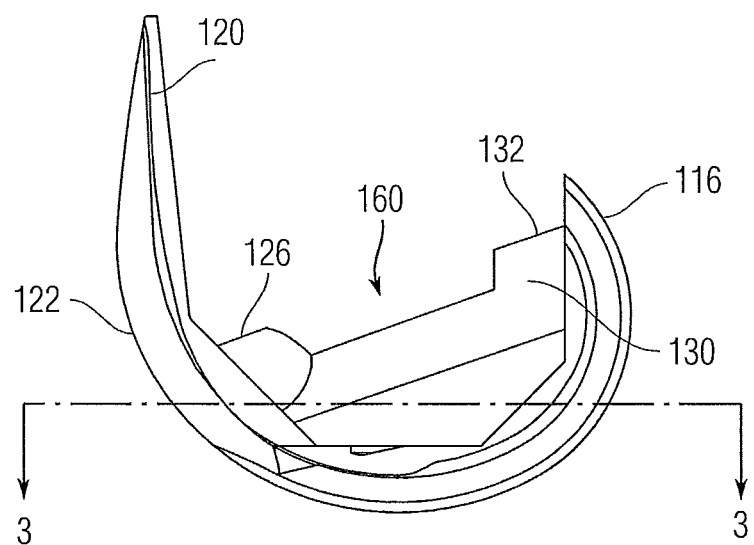
FIG. 2 is a side view of the femoral component of FIG. 1.

The present invention is directed to there is a need for prosthetic condylar joints with articulating bearing surfaces having a translating contact point during rotation (varus/valgus) thereof. The teachings of the present invention can therefore generally be applied to any prosthesis that is intended for in a condylar type joint, such as the knee, elbow, ankle, etc.

Constrained Condylar Knee Implant

FIGS. 1-30 illustrate a joint prosthesis, in the form of a knee joint prosthesis 100, according to several exemplary embodiments of the present invention. The illustrated prosthesis 100 is of a constrained condylar knee (CCK) implant type.

The prosthesis 100 generally includes a femoral component 110 (FIGS. 1-4) for attachment to the femur and a tibial component 200 (FIGS. 9-13) for attachment to the tibia. The femoral component 110 is formed of a body 112 that has a pair of laterally spaced-apart femoral condylar portions 114, 116, each of which is smoothly convexly curved in a lateral profile generally to approximate the curvature of an anatomical femoral condyle and is convexly curved along its anteroposterior extent. The anterior parts of the condylar portions merge smoothly with convexly curved lateral portions 122 of a patellar portion 120. A midportion 126 of the patellar portion 120 intersects at its inferior extremity a superior wall or roof 132 of a box-like intercondylar portion 130 (stabilizer box), which together with the patellar portion 120, connects the condylar portions 114, 116.

As described in detail in commonly assigned U.S. patent application Ser. No. 11/860,423 (U.S. patent publication No. 2008/0097615) (which is hereby incorporated by reference in its entirety), the design of the intercondylar portion 130 has been modified so that the amount of bone that has to be removed is reduced.

The intercondylar portion 130 is defined by an arcuate shaped wall 131 that likewise defines the roof 132 of the portion 130. The roof 132 can thus be thought of as the apex region of the arcuate shaped wall 131. The illustrated arcuate shaped wall 131 has a semi-circular shape or "rounded shape" that is designed to be received within a complementary rounded bone notch or opening. The present intercondylar design thus does not include a well defined roof that is generally horizontal (parallel to a nominal base plane). Significantly less bone is removed in the design of the present invention since the hard squared edges of the conventional femoral box notch are absent in the rounded femuoral box notch made according to the present invention. The cylindrical shape of the femoral box notch made in the femur can be cut with a rotating cutter, such as a drill or reamer, which eliminates the additional stress concentrations created by the overcut slots that are created when cutting the box geometry with a sagittal saw. In other words, the cylindrical box geometry can be cut without creating stress concentrations in the corners where a sagittal saw would extend the cut past the edge of the box.

Figure 3:
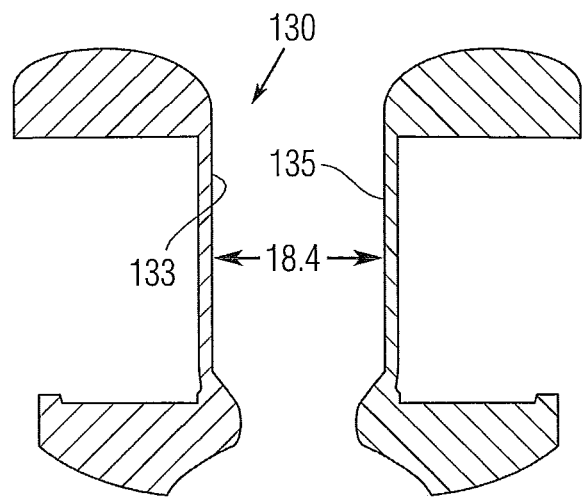
FIG. 3 is a cross-sectional view taken along the line 3-3 of FIG. 2.

The femoral component 110 can be made of a number of different materials, including a surgical grade, durable metal, such as a 316L stainless steel or a chrome-cobalt-molybde- Straight Box Femoral Component FIGS. 1-4 show the femoral component 110 according to one embodiment. The femoral component 110 according to this embodiment can be referred to as having a straight box. The intercondylar portion 130 (stabilizer box) includes a first inner wall 133 and an opposite second inner wall 135 that terminate at the roof structure of the box. In this first embodiment, the two inner walls 133, 135 are parallel to one another as shown in FIG. 3. FIG. 3 thus shows the distance between the inner walls 133, 135 as being uniform along the length of the walls 133, 135.

Figure 4:
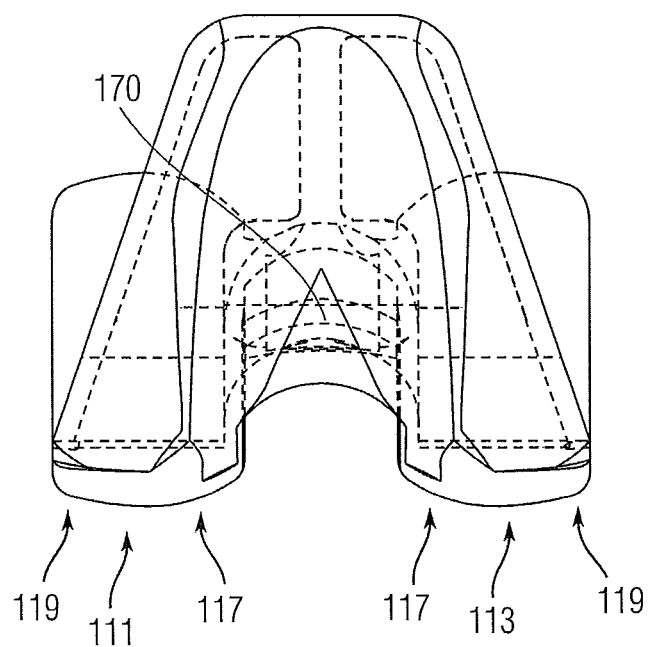
FIG. 4 is an end view of the femoral component of FIG. 1.

In yet another aspect of the present invention and as described herein, in the present invention, the shape of the femoral component 110 (as well as the tibial component 200) has been modified so that the geometry is no longer a swept circular shape (i.e., a toroid). Instead, the swept geometry consists of two tangent radii, for which the medial radius of the condyle is smaller than the lateral radius. More specifically, an underside of the femoral component 110 includes a first condylar bearing surface 111 and a second condylar bearing surface 113. FIG. 4 generally shows the medial radius 117 of each condylar bearing surface 111, 113 and the lateral radius 119 of each condylar bearing surface 111, 113, with the medial radius 117 being less than the lateral radius 119.

In yet another embodiment, each of the condylar bearing surfaces 111, 113 can be formed by a surface that is created with a multiple radius curve (spline) where the medial part of the curve has smaller radii than the lateral part. Thus, the surface can be defined by more than two radii.

Stepped Box Femoral Component

Figure 5:
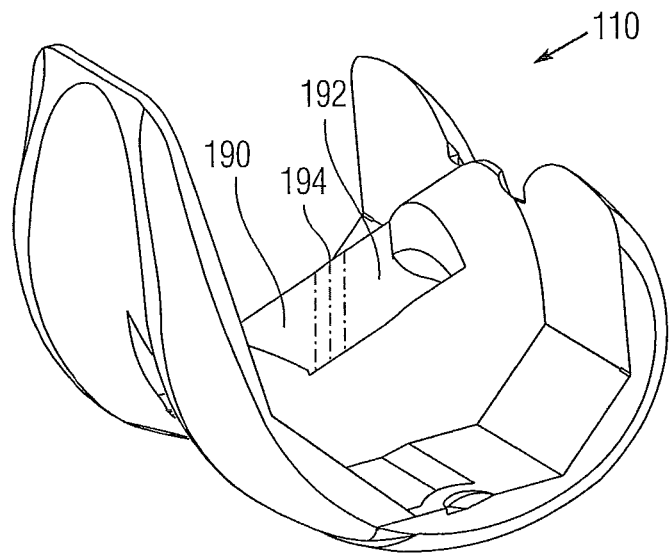
FIG. 5 is a side perspective view of a femoral component, according to a second embodiment.
Figure 6:
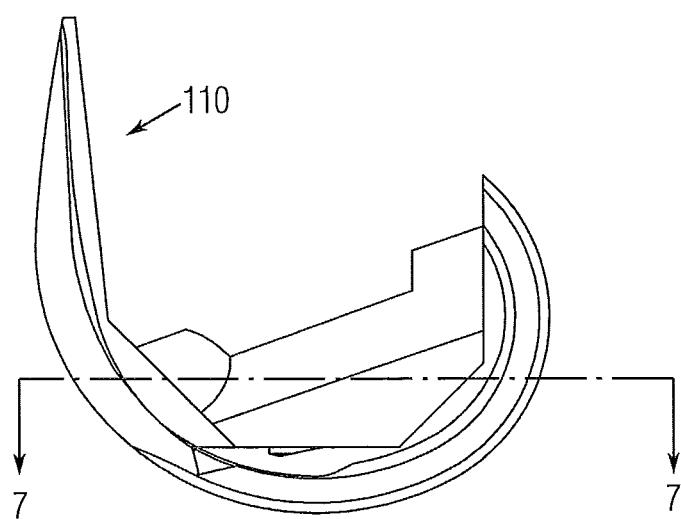
FIG. 6 is a side view of the femoral component of FIG. 5.

FIGS. 5-8 illustrate a femoral component 110 according to another embodiment. The femoral component 110 of FIGS. 5-8 is very similar to the femoral component 110 of FIGS. 1-4 in that it includes first and second condylar bearing surfaces 111, 113 that each is formed and defined by at least two tangent radii. The difference between the femoral component 110 of FIGS. 5-8 and the femoral component 110 of FIG. 1-4 is that the first inner wall 133 and an opposite second inner wall 135 are not completely parallel walls (relative to one another and from end to end) but instead, the walls 133, 135 have at least have one section that has a non-parallel orientation relative to an opposing section of the other wall. As shown in FIG. 5, each of the walls 133, 135 includes a first section 190 (anterior portion) at one end of the wall 133, 135 and a second section 192 (posterior portion) at the opposite end of the wall 133, 135, with a third section 194 being a transition portion that is located between the first section 190 and the second section 192. The distance between the opposite walls 133, 135 varies depending upon the location along the length of the walls 133, 135.

In one embodiment, the walls 133, 135 have a stepped construction in that the first sections 190 are parallel to one another and similarly, the second sections 192 are parallel to one another; however, the distance between the first sections 190 is different than the distance between the second sections 192. The third section 194 is a region that is not-parallel to the other third section 194 and instead is a region where the wall has a sloped surface.

Figure 7:
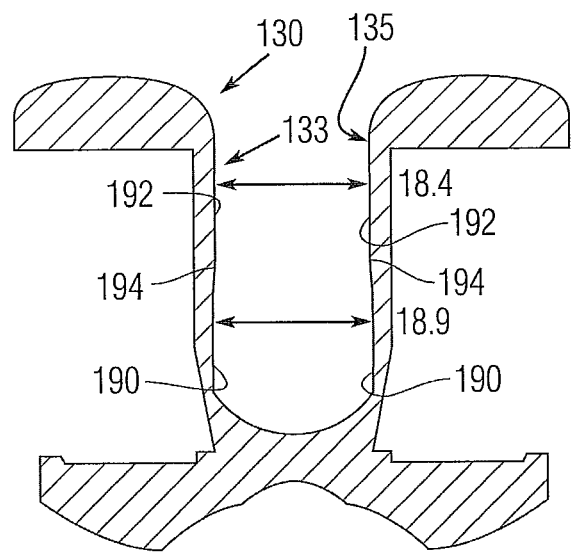
FIG. 7 is a cross-sectional view taken along the line 7-7 of FIG. 6.
Figure 8:
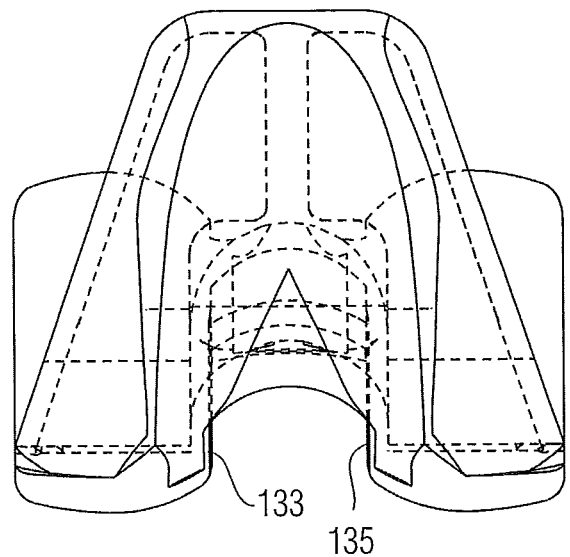
FIG. 8 is an end view of the femoral component of FIG. 5.
Figure 9:
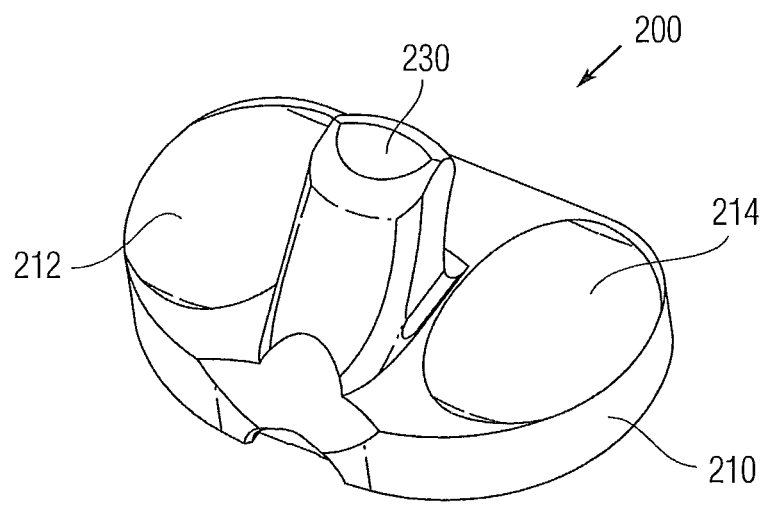
FIG. 9 is an end and side perspective view of a tibial component that forms a part of a knee joint prosthesis.
Figure 10:
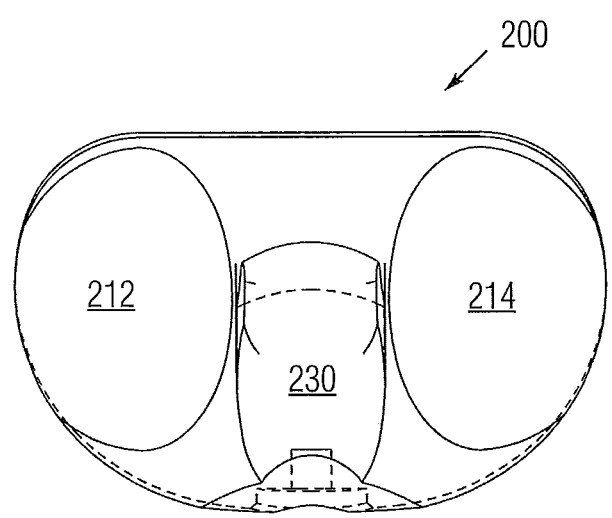
FIG. 10 is a top plan view of the tibial component of FIG. 9.
Figure 11:
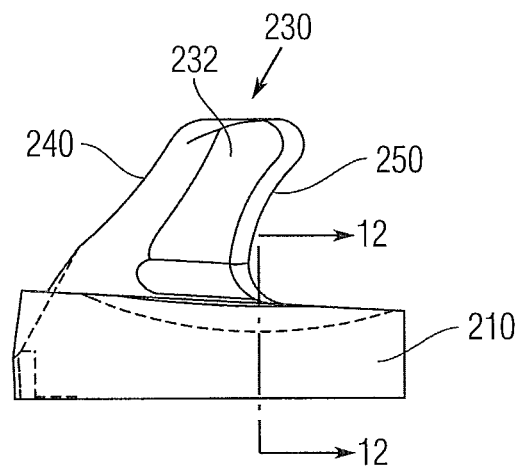
FIG. 11 is a side elevation view of the tibial component of FIG. 9.

In the illustrated embodiment, the anterior portion of the box is wider than the posterior portion and accordingly, the distance between the first sections 190 is greater than the second sections 192 as shown in FIG. 7.

Figure 29:
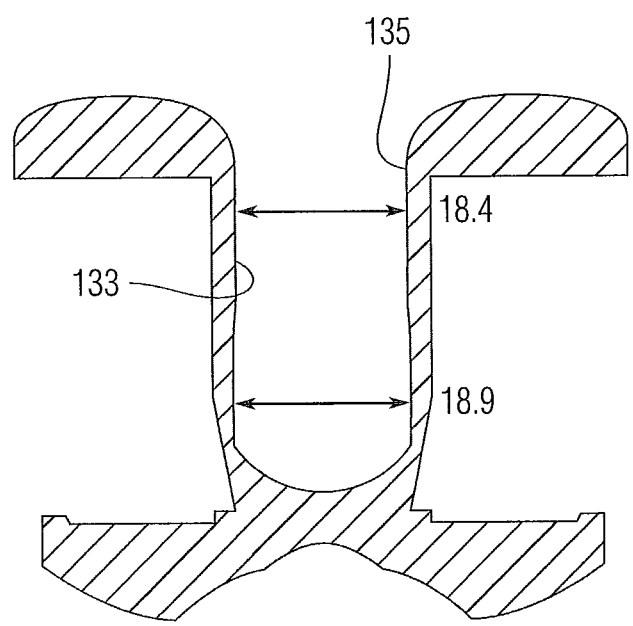
FIG. 29 is a cross-sectional view of the femoral component showing a tapered intercondylar box.

In another embodiment shown in FIG. 29, the walls 133, 135 can have a tapered construction in that the walls 133, 135 are not parallel but instead are oriented in a converging orientation. The walls 133, 135 can each have a smooth appearance with the distance between the walls 133, 135 becoming progressively greater in the anterior direction. Thus, as in the previous embodiment, the anterior portion represents the widest portion of the box.

Tibial Component

Now referring to FIGS. 9-12, the prosthesis 100 includes tibial component 200. The tibial component 200 is part of a tibial assembly that includes a tibial platform or tray (not shown) from which a tibial stem extends downwardly and is constructed for insertion and attachment to the tibia. An upper surface of the tibial tray is constructed to receive and attach to a bearing component 200 (tibial insert) that is positionable between the femoral component 110 and the tibial tray. As described in greater detail below, the tibial insert 220 cooperates with the femoral component 110 to provide for the desired kinematics of the knee prosthesis.

As shown in the figures, the tibial component 200 includes an oblong, rounded, disc-like plateau portion 210 that has an upper surface that can be flat or have some other predetermined contour. A pair of laterally spaced-apart, oblong concavities 212, 214 is formed along the upper surface for receiving femoral condylar portions 114,116 of the femoral component 110 as described below. The "nested" support of the femoral component 110 stabilizes the prosthetic joint, but still permits antero-posterior translation, lateral angulation and rotation, all of which are involved in normal function of the anatomical knee joint.

The tibial insert 220 also preferably includes a base-like fixation portion that extends from a bottom surface of the plateau portion 210 to allow the tibial insert 220 to be attached to the tibial tray using conventional techniques and methods.

The tibial insert 220 also includes a stabilizing post 230 that extends upward from the plateau portion 210 between the concavities 212, 214 and is positioned to be received in an intercondylar recess of the femoral component 110. The stabilizing post 230 is generally triangular in a lateral profile and is defined by side surfaces 232, an anterior face 240, and an opposite posterior face 250. The side surfaces 232 of the stabilizing post 230 are in sufficient clearance from the lateral walls of the femoral intercondylar recess to allow for normal lateral angulation and rotation when assembled with the femoral component 110 of the prosthetic knee joint. Exemplary constructions of the posterior face 250 and anterior face 240 of the stabilizing post 230 are described in the '615 publication.

Figure 12:
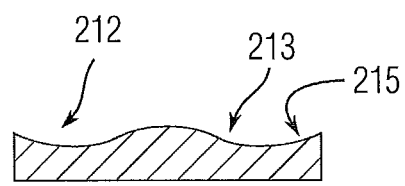
FIG. 12 is a cross-sectional view taken along the line 12-12 of FIG. 11.

As mentioned above, the pair of laterally spaced-apart, oblong concavities 212, 214 is formed along the upper surface for receiving femoral condylar portions 114,116 of the femoral component 110 and therefore, have complementary shapes relative to the condylar portions 114, 116. Accordingly and similar to the femoral component 110, the contact bearing surfaces 212, 214 of the tibial component 200 do not have swept circular shape (i.e., a toroid) but instead, the swept geometry consists of at least two tangent radii (curved articular geometry). FIG. 12 illustrates the swept geometry of each of the bearing surfaces 212, 214 and in particular and in accordance with the illustrated embodiment, each bearing surface 212, 214 has a first radius (medial or inner) 213 and a second radius (lateral or outer) 215, with the medial radius 213 being less than the lateral radius 215. This design is complementary to the design of the bearing surfaces of the femoral component 110 and therefore, when the two mate together, the reduced medial radii portions of the component overlie one another and lateral radii portions of the components overlie one another.

The ratio of femoral to tibial radii is approximately 0.85 to 0.95.

Tapered Stabilizing Post

Figure 13:
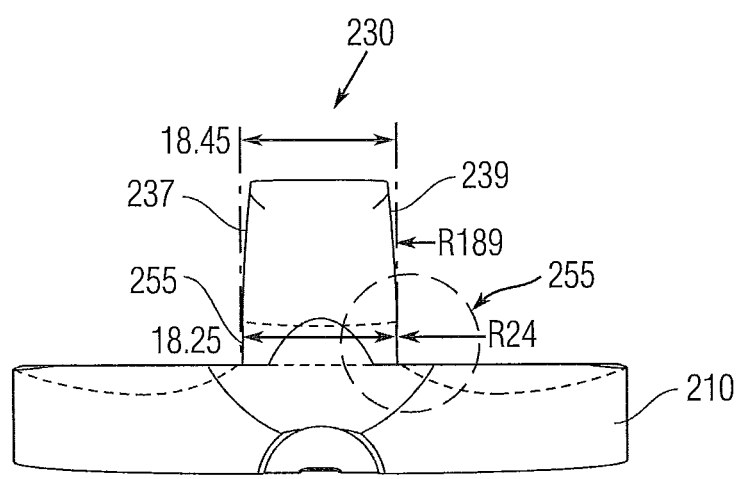
FIG. 13 is an end view of the tibial component.

With reference to FIG. 13, the geometry of the tibial post has been modified from current designs to reduce local deformation of the tibial post 230. Conventional tibial posts have flat medial and lateral faces. In contrast, the post 230 of a tibial component according to one embodiment of the present invention has been replaced by faces that are slightly curved. Opposing first and second (medial and lateral) faces 237, 239, respectively, of the post 230 are not flat (parallel to one another) but instead, the faces 237, 239 are curved. As shown in FIG. 13, in a direction toward the top of the post 230, the opposing faces 237, 239 diverge from being parallel to one another and are inwardly tapered toward one another.

In the illustrated embodiment, the faces 237, 239 have a radius of about 189 mm; however, it will be appreciated that this value is merely exemplary in nature and the faces can be formed to have a curvature defined by a radius having a different value.

As a result of the curved nature of the post 230 and as the femoral component 110 rotates, contact with the post 230 occurs over a broader surface than if the post 230 were flat as in the case of conventional posts.

Figure 20:
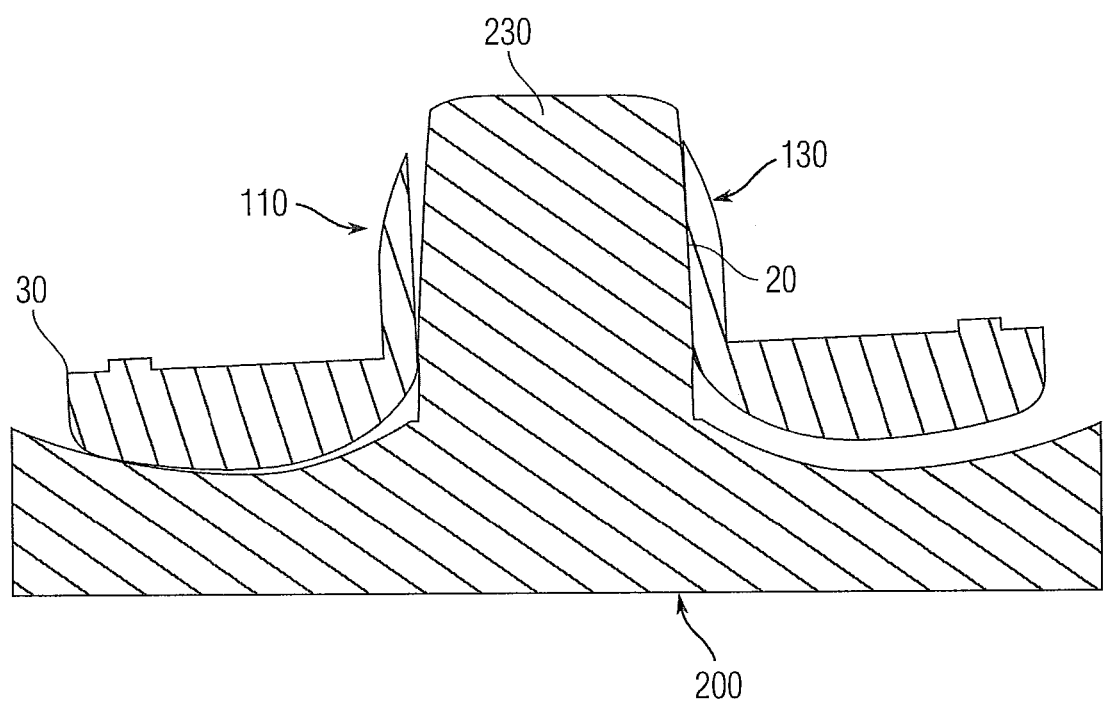
FIG. 20 is a cross-sectional view taken along the line 20-20 of FIG. 18.

Also, as shown in FIG. 13, a slight recess 255 has been built into the tibial post 230 at a lower portion thereof to reduce contact between the inside edge of the femoral component 110 and the tibial post 230. In effect, the recess 255 can be a slightly shaved region of the post 230. This "relief" feature is shown in FIG. 20. In addition, the contact of the post against the intercondylar box guides prevents the femoral component from sliding back medially, therefore maintaining the improved varus/valgus stability when the knee is rotated in the coronal plane.

Figure 30:
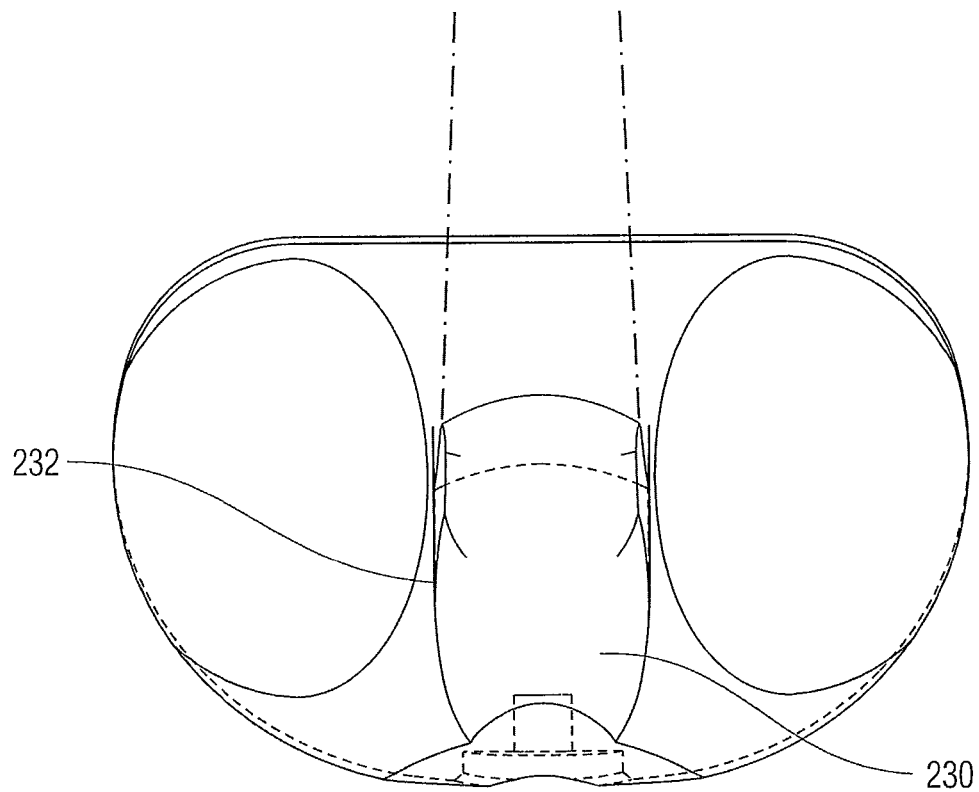
FIG. 30 is a top plan view of a tibial insert with a stabilizing post having a tapered design according to another embodiment.

As mentioned above, in one embodiment (FIG. 29), the walls 133, 135 of the intercondylar box have a tapered construction (the anterior portion represents the widest portion of the box) and similarly, as shown in FIG. 30, the walls 232 of the post 230 can have a complementary design to mate with the tapered walls 133, 135. More specifically, the post 230 has a complementary tapered shape as shown in the figure. This permits proper and complementary reception of the post within the box and engagement of the respective tapered surfaces.

Improved Varus/Valgus and Anterior-Posterior Stability

As described herein, the prosthesis 100 according to the present invention consists of a modified femoral component 110 of either a straight box configuration (FIGS. 1-4) or a stepped or tapered box configuration (FIGS. 5-8) and a complementary, mating tibial component (tibial insert) 200. The present design improves the stability of the prosthesis 100 (CCK device) by using the condylar articulation of the knee implant 100 acting in concert with the central post 230 to provide both varus/valgus and anterior-posterior stability.

A primary stabilizer of the knee to varus/valgus rotation is the ability of the knee to transfer more load from one condyle to the other and, under more extreme loads, to lift off and load a single condyle when rotated in the coronal plane. This stabilization occurs with the natural knee as well as any bicondylar knee implant. However, in a typical bicondylar implant, where the femoral component has toroidal geometry, the contact point between the femoral component and tibial component tends to stay at the center of the condyle, especially when the joint is under compressive axial load.

Figure 14A:
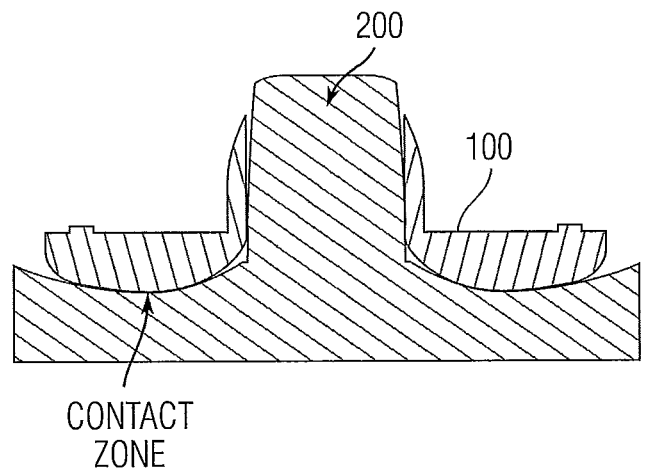
FIGS. 14A and 14B are cross-sectional views of the femoral component mated with the tibial component in different orientations showing migration of a bearing contact point between the two components when the knee joint prosthesis has undergone varus/valgus rotation.
Figure 14B:
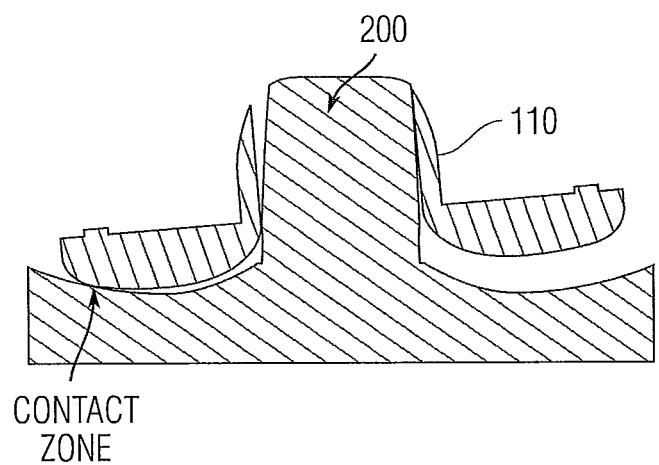

In accordance with the present invention, the modified shape of the femoral component 110 and tibial component 200 so that the geometry is no longer a swept circular shape (i.e., a toroid). Instead, the swept geometry consists of the two tangent radii described above, for which the medial radius of the condyle is smaller than the lateral radius. It will therefore be appreciated that both the femoral component 110 and the tibial component 200 have this complementary geometry. As the knee rotates into varus or valgus, the contact point between the two components 110, 200 shifts away from the center of the knee (in an outward (lateral) direction), and thus the restoring moment generated by contraction of the quadriceps and/or hamstring muscles increases. FIGS. 14A and 14B show the shifting nature of the contact point. In FIG. 14A, the contact point between the femoral component 110 and the tibial component 200 is indicated by the arrow. FIG. 14B shows that when the knee undergoes varus/valgus rotation, the contact point (as indicated by the arrow) between the femoral component 110 and the tibial component 200 shifts and more specifically, shifts in a direction away from the center. In other words, the design of the femoral component 110 and the tibial component 200 provide for a translating bearing contact point (in the lateral/outward direction) between the femoral component 110 and the tibial component 200 as the knee undergoes varus or valgus rotation.

Figure 15:
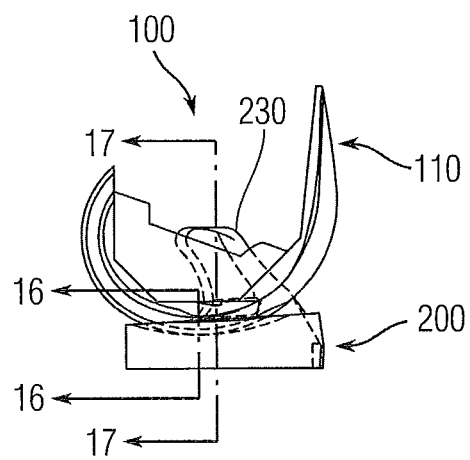
FIG. 15 is a side elevation view showing the conformation of the femoral component of FIG. 1 with the tibial component at 0 degrees rotation and full extension (0 degrees flexion)
Figure 16:
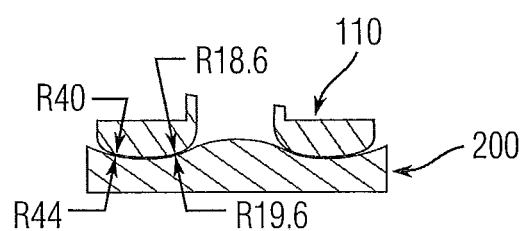
FIG. 16 is a cross-sectional view taken along the line 16-16 of FIG. 15.
Figure 17:
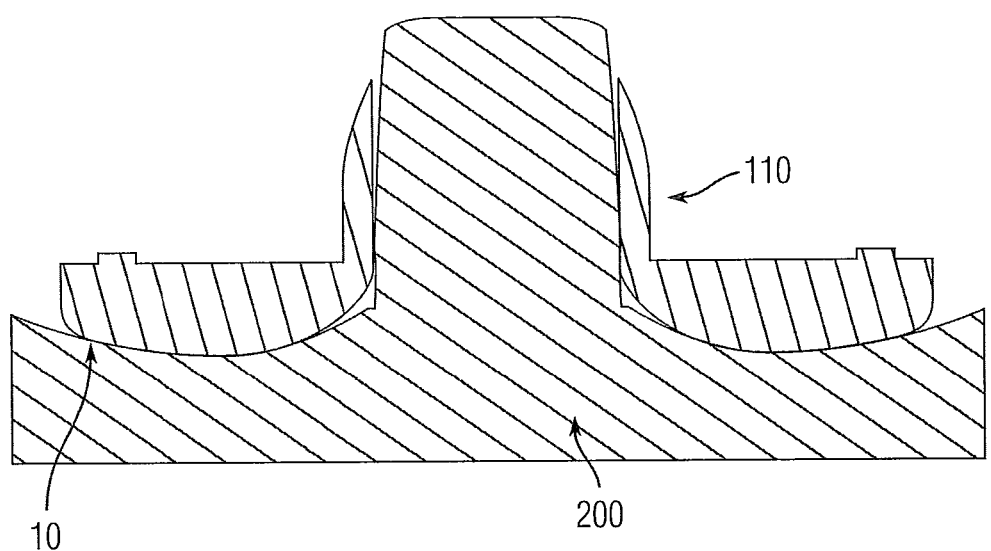
FIG. 17 is a cross-sectional view taken along the line 17-17 of FIG. 15.

FIGS. 15-17 illustrate the conformation of the femoral component 110 (straight box embodiment of FIGS. 1-4) with the tibial component 200 at 0 degrees rotation and full extension (flexion). In FIG. 16, the multi radii construction of the femoral component 110 and the tibial component 200 is shown.

In addition, as shown in FIG. 17, there is a slight clearance that exists between the lateral condylar portion of the femoral component 110 and the lateral tibial component 200 when the knee is in 0° of rotation. The clearance is indicated at reference character 10.

Based on the geometry of a standard size knee, the contact point can be lateralized by approximately 15 mm. However, it will be appreciated that this value is merely exemplary in nature and other values are equally possible depending upon the construction of the device. Shifting the contact force location laterally can increase the restoring moment of the knee by approximately 70%.

Figure 18:
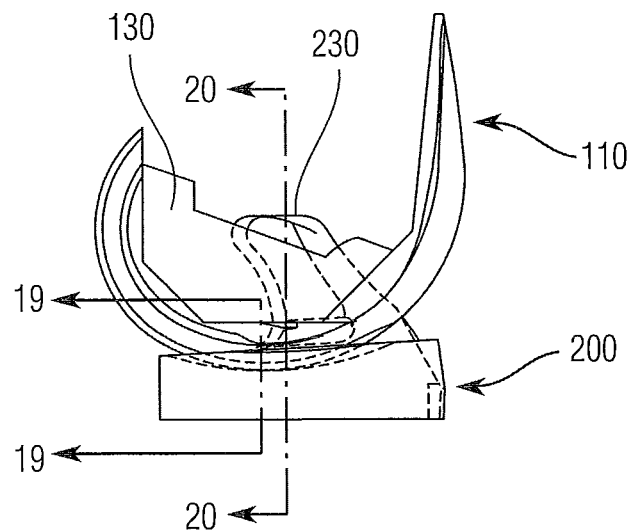
FIG. 18 is a side elevation view showing the conformation of the femoral component (FIG. 1) with the tibial component at 2 degrees rotation and full extension (0 degrees flexion)
Figure 19:
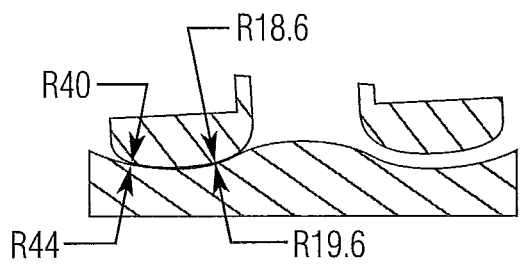
FIG. 19 is a cross-sectional view taken along the line 19-19 of FIG. 18.

FIGS. 18-20 illustrate the conformation of the femoral component 110 (straight box configuration of FIGS. 1-4) with the tibial component 200 at 2 degrees rotation and full extension. It will be appreciated that at about 2° of rotation, the post 230 contacts the box 130 of the femoral component 110, and the post/box articulation provides additional constraint to varus/valgus rotation as shown in FIG. 20. In FIG. 19, the multi radii construction of the femoral component 110 and the tibial component 200 is shown and indicated by the reference characters. In FIG. 20, the point of contact between the post 230 and the box 130 is shown at reference character 20, while contact between the condylar portion of the femoral component 110 and the tibial component 200 is indicated at reference character 30.

By shifting the contact point laterally (outwardly) (see FIGS. 14A and 14B), the knee stability (i.e., stiffness) gradually increases. Then, as the curved post 230 accepts more of the load, the varus/valgus stiffness of the knee further increases. This gradual increase in stiffness is in contrast to conventional CCK implants where once the knee lifts off, the stiffness remains relatively constant. The shifting bearing contact point provides a CCK implant design that overcomes the deficiencies of the conventional CCK implants.

While there are existing knee systems that have articular geometry that is not toroidal, these systems employ a nearly flat on flat configuration in the coronal plane. These designs will lateralize the contact point upon varus/valgus loading.

The difference between these conventional designs and the present design is that with the curved articular geometry of the present prosthesis 100, the contact point shifts laterally in a gradual manner. In this way, the stiffness of the knee increases gradually, rather than increasing in a step-wise fashion after liftoff. In addition, a design that immediately lateralizes the contact point, as in the conventional devices, is at a greater risk for extreme edge loading of the tibial insert, putting the polyethylene implant, the fixation to the underlying bone, and the bone itself at risk.

Varus/Valgus Stability in Mid-Flexion

As described herein, in the embodiment shown in FIGS. 5-8, the femoral component 110 can be modified to have a step-off on the surfaces 131, 133 of the box of the femoral component 110. When the femur is in extension rotated into varus/valgus, the contact between the post and the femoral component 110 occurs at the wider, anterior portion of the box.

Figure 21:
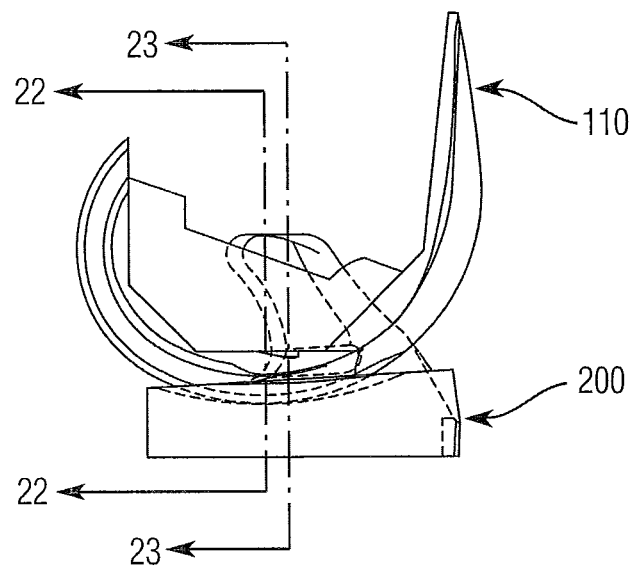
FIG. 21 is a side elevation view showing the conformation of the femoral component (FIG. 5) with the tibial component at 5 degrees rotation and full extension (flexion)
Figure 22:
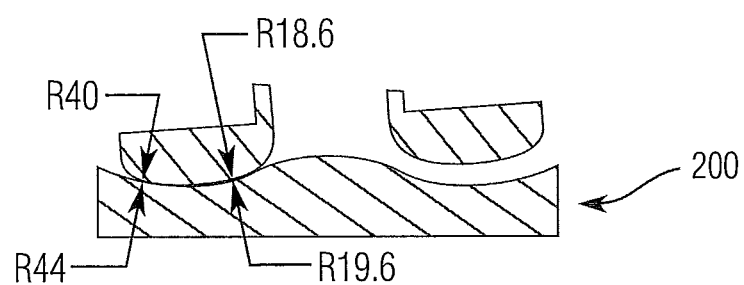
FIG. 22 is a cross-sectional view taken along the line 21-21 of FIG. 20.
Figure 23:
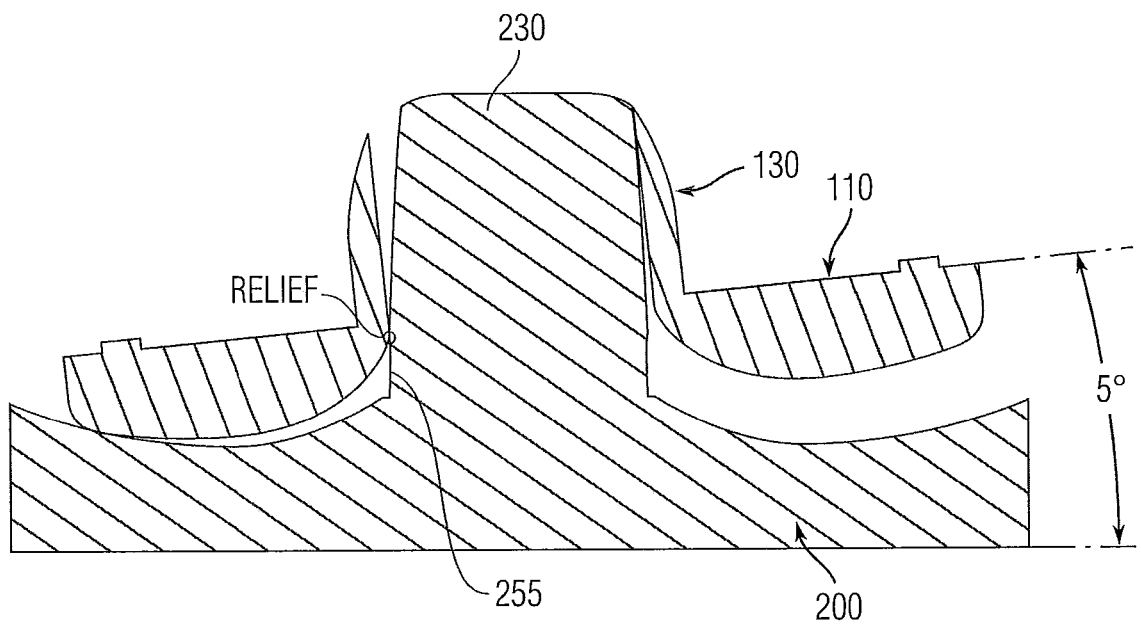
FIG. 23 is a cross-sectional view taken along the line 22-22 of FIG. 20.
Figure 24:
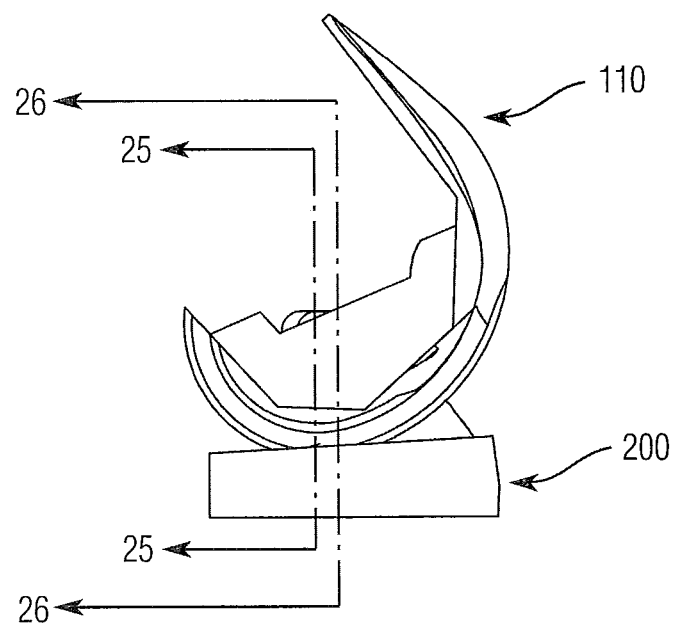
FIG. 24 is a side elevation view showing the conformation of the femoral component (FIG. 5) with the tibial component at 2 degrees rotation and 45 degrees flexion.
Figure 25:
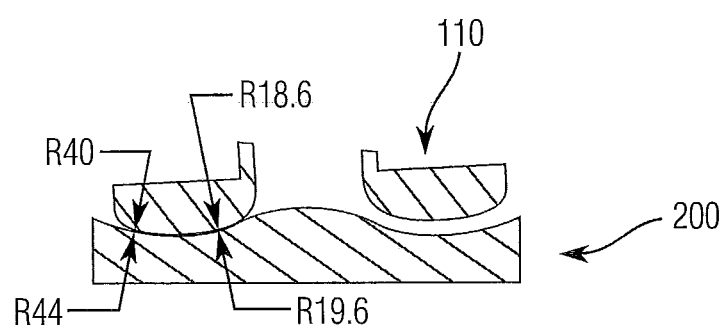
FIG. 25 is a cross-sectional view taken along the line 25-25 of FIG. 24.
Figure 26:
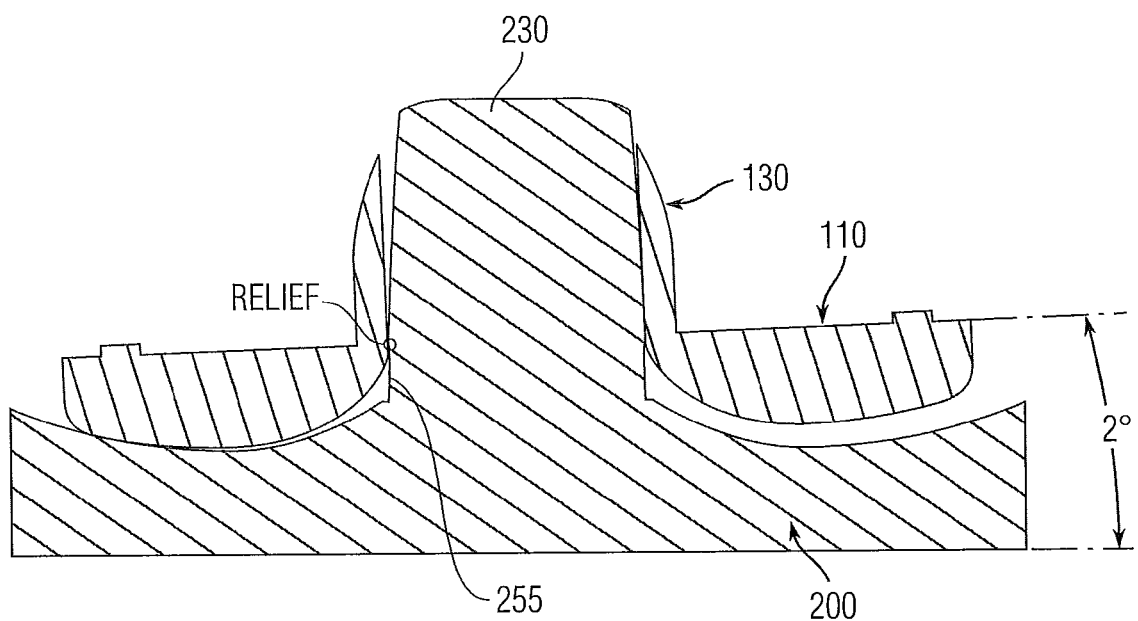
FIG. 26 is a cross-sectional view taken along the line 26-26 of FIG. 24.

FIGS. 21-23 show the conformation of the femoral component 110 (stepped box design of FIGS. 5-8) with the tibial component 200 at 5 degrees rotation and full extension, thereby causing the contact point to move laterally. In FIG. 22, the multi radii construction of the femoral component 110 and the tibial component 200 is shown and indicated by the reference characters. FIGS. 24-26 show the conformation of the femoral component 110 (stepped box design of FIGS. 5-8) with the tibial component 200 at 2 degrees rotation and full extension.

The wider box configuration, due to the stepped wall or tapered wall construction, permits greater rotation until contact is made between the post 230 and the box 130 (in this embodiment, approximately 5° of rotation as shown in FIG. 23). Relief provided by recessed section 255 is also shown in FIG. 23. As shown in FIGS. 24-26, when the femur is in the mid-flexion position (about 45° of flexion) and rotated into varus/valgus, the contact between the post 230 and the femoral component 110 occurs at the posterior, narrower portion of the box 130 as best shown in FIG. 26. At this location, only 2° of rotation can occur before contact between the post 230 and the box 130.

Figure 27:
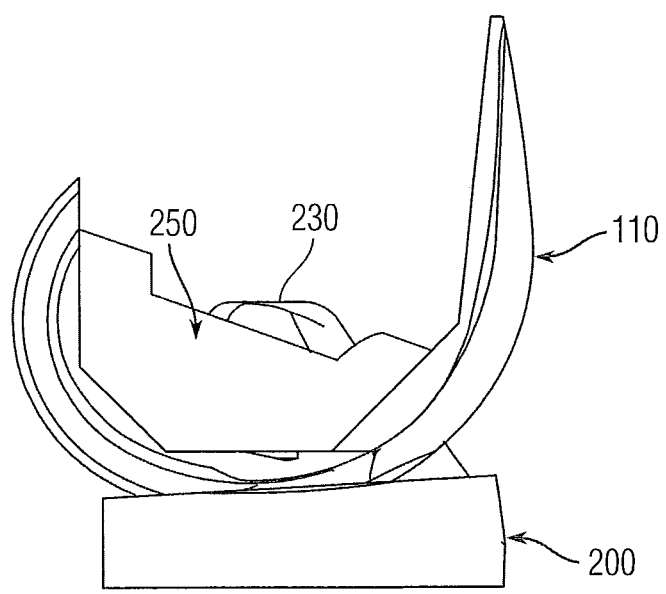
FIG. 27 is a side elevation view showing the conformation of the femoral component (FIG. 5) with the tibial component at zero degrees flexion.
Figure 28:
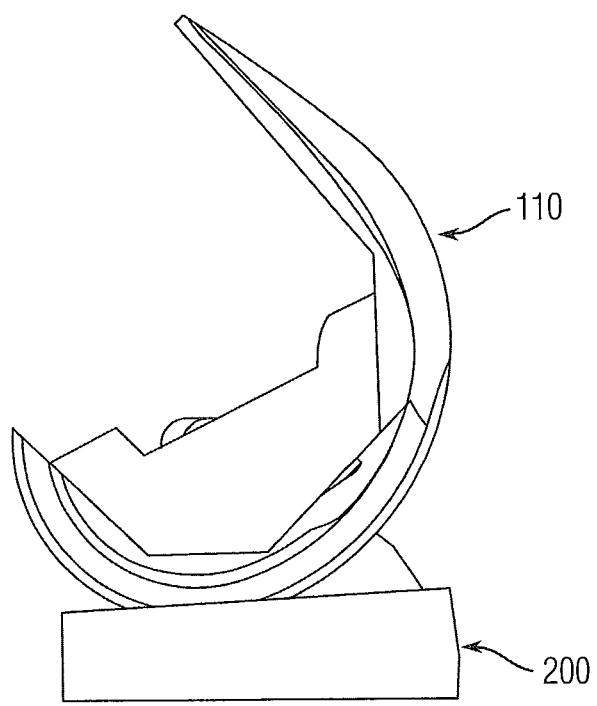
FIG. 28 is a side elevation view showing the conformation of the femoral component (FIG. 5) with the tibial component at 45 degrees flexion.

To reduce the amount of anterior translation of the knee at near full extension, the proximal posterior surface, as indicated at 250, of the post 230 has been extended posteriorly as shown in FIGS. 27 and 28. The additional posterior material reduces anterior translation by approximately 5 mm. The extension of material is only included on the upper portion of the post 230 so the kinematics of the post/cam articulation is not affected during flexion.

It will be appreciated that the present invention is suitable for revision knee replacement or primary knee replacement for patients with poor collateral ligaments (e.g., extreme valgus deformity). The improved designs of the bearing surfaces of the implant components provide improved stability and performance of the joint during rotation (varus/valgus). The modified surface geometry of the present components provides a better match to patient anatomic requirements through a full range of motion (flexion-extension and rotations).

It will be appreciated that any numerals or values set forth in the drawings represent exemplary dimensions and only unless otherwise mentioned, in the metric unit of millimeters.

Elbow Implant System

In accordance with another embodiment, the teachings of the present invention can be applied to an elbow prosthesis.

The elbow system can be either of a linked type or unlinked type in that a humeral component can either be linked to an ulnar component or they can be unlinked and free of attachment. For example, FIG. 31 is a perspective view of an illustrative modular, unlinked elbow replacement device in accordance with some embodiments of the disclosed subject matter and FIG. 32 is a perspective view of an illustrative modular, linked elbow replacement device in accordance with some embodiments of the disclosed subject matter.

Details of the various components that make up both the linked and unlinked elbow systems are set forth in the '575 application that has been incorporated herein.

Unlinked Ulnar Bearing Component

Figure 31:
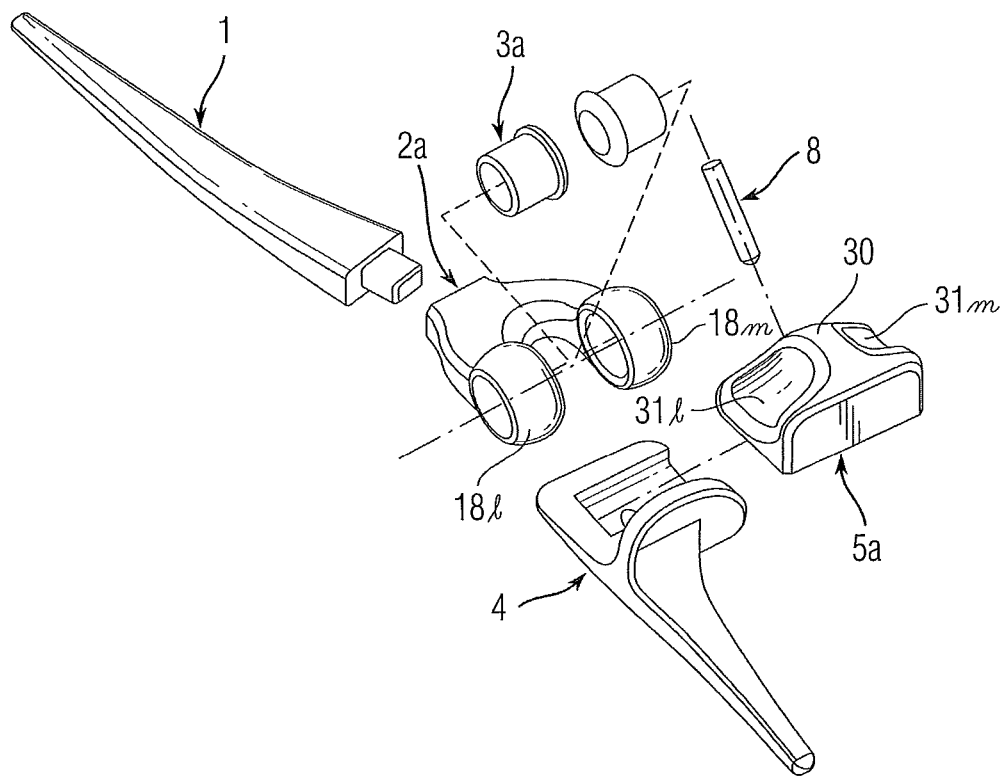
FIG. 31 is a perspective view of an illustrative modular, unlinked elbow replacement device in accordance with some embodiments of the disclosed subject matter.
Figure 32:
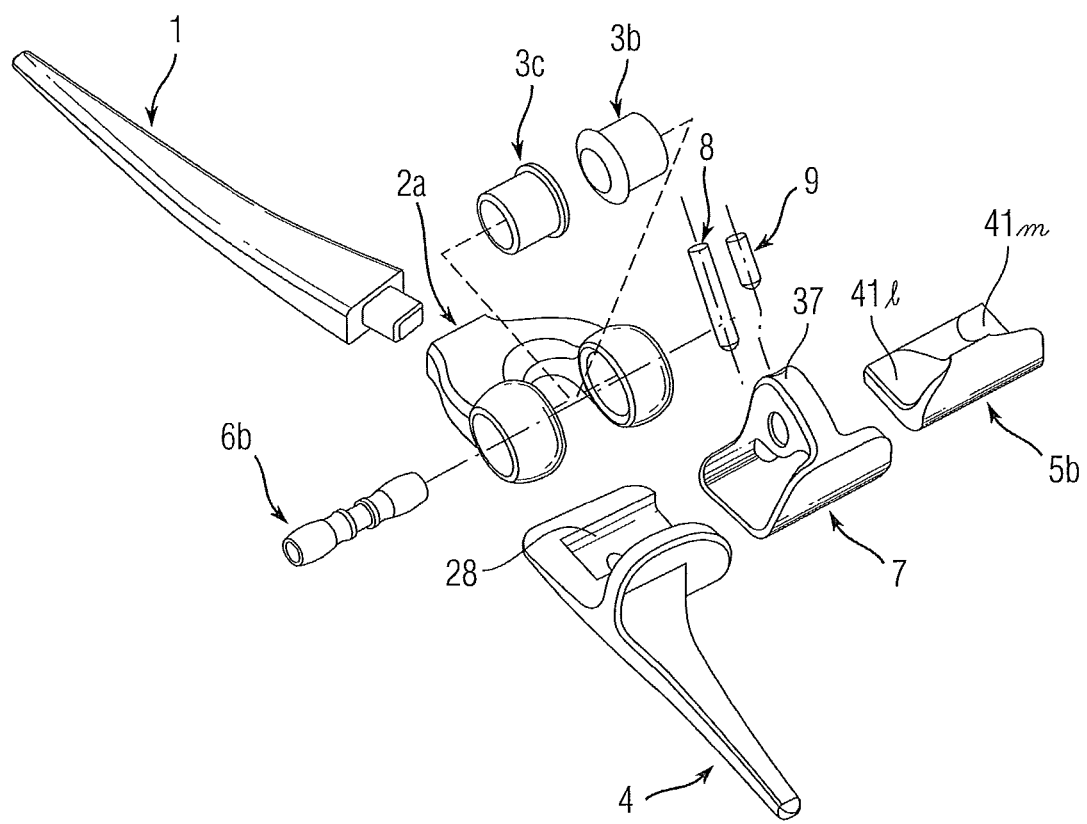
FIG. 32 is a perspective view of an illustrative modular, linked elbow replacement device in accordance with some embodiments of the disclosed subject matter.

However, generally, the unlinked elbow system of FIG. 31 includes a humeral stem 1 that can be detachably connected to a humeral condylar component 2a that has distally extending portions (medial $18_M$ and lateral $18_L$ condyles) that are separated from one another. The humeral condylar component 2a is designed to engage complementary bearing surfaces that are part of an ulnar implant assembly. For example, an unlinked ulnar bearing component 5a can have an engagement feature that interacts with a sliding capture mechanism of an ulnar stem 4 for detachably coupling the ulnar bearing component 5a to the ulnar stem 4. In one embodiment, the ulnar bearing component 5a can be inserted from approximately the medial and/or lateral direction. The bearing component 5a can be rigidly locked to the stem 4 using, for example, a locking component 8.

The unlinked ulnar bearing 5a has two concave surfaces $31_{M,L}$ that articulate with the convex humeral condyles $18_{M,L}$. The medial surface $31_M$ may have a greater width ($W_{UM}$) than lateral surface $31_L$ ($W_{UL}$), improving load transfer on the medial side. The articulation is non-conforming. The bearing 5a also has a central post 30 that provides medial-lateral stability and a raised, distal articular face to resist posterior dislocation of the ulna in flexion. The post 30 may be rectangular or trapezoidal in shape. The articulation-adjustability of ulnar stem 4 allows a surgeon to select ulnar bearings 5a of varying sizes/options defined by post thickness and/or bearing thickness γ for intra-operative adjustment of the degree of constraint, and/or various post alignments to adjust carry angle. The unlinked ulnar bearing 5a may be made of a low friction material, for example, ultra-high molecular weight polyethylene (UHMWPE).

Linked Ulnar Bearing Component

In another embodiment, shown in FIG. 32, a linked ulnar assembly is provided and includes a linked ulnar bearing housing 7 that can have an engagement feature that interacts with a sliding capture mechanism 28 of the ulnar stem 4. The housing 7 has a central post 37 that provides medial-lateral stability of the linked elbow system. The housing 7 has a first opening to accept a linked ulnar bearing 5b from a medial and/or lateral direction. The linked ulnar bearing 5b has two concave surfaces $41_{M,L}$ that articulate with the convex humeral condyles $18_{M,L}$. The medial surface $41_M$ may have a greater width ($W_{Mu}$) than lateral surface $41_L$ ($W_{Lu}$), improving load transfer on the medial side. The articulation is non-conforming.

Figure 36:
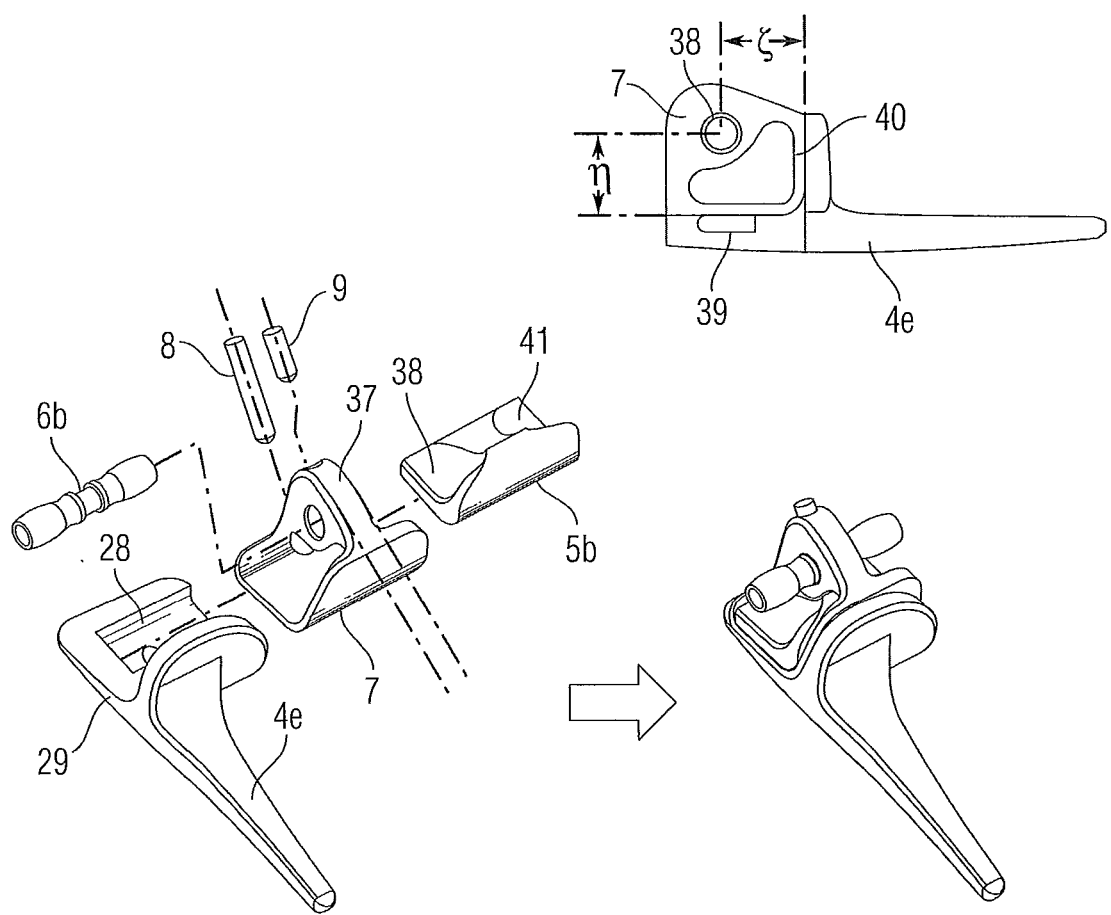
FIG. 36 provides a perspective view of an ulnar stem, linked ulnar bearing, and linked ulnar bearing housing in accordance with some embodiments of the disclosed subject matter.

The bearing 5b can either be rigidly locked to central post 37 using, for example, a locking component 8, or act as a sliding platform with respect to central post 37. Should the bearing 5b need to be replaced, it can be removed from a medial or lateral direction. The linked ulnar bearing 5b may be made of a low friction material, for example, ultra-high molecular weight polyethylene (UHMWPE). The elbow replacement system provides various housing options. The post thickness c and/or bearing thickness options permit intra-operative adjustment of the degree of constraint. As shown in FIG. 36, the post 37 has a second opening 38 for axle 6. The axle hole 38 location option allows the surgeon to adjust anterior-posterior q and/or superior-inferior 4 offset of the joint axis 12. The axle 6 can be assembled from the medial and/or lateral direction to the central post 37 in vivo. The axle 6 can be rigidly locked to housing 7 using, for example, a locking component 9. The central portion 6c of axle that mates with housing 7 can have a D-shaped cross-section to prevent rotation about the joint axis 12. The central portion 6c may have a stop to prevent the central portion from advancing beyond central post 37. The ends 34 of the axle articulate with the inner diameters of the humeral bushings 3b,c.

Non-Confirming Articulation Between Humeral and Ulnar Bearing Components

Figure 33:
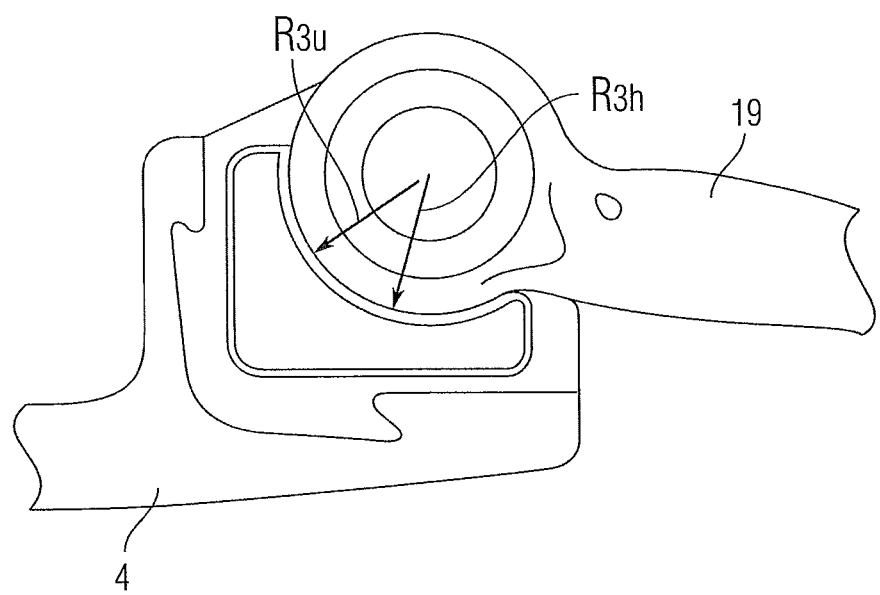
FIG. 33 illustrates differences in articular geometry between the humeral condyles and ulnar bearing surfaces in accordance with some embodiments of the disclosed subject matter.

Similar to the CCK device described hereinbefore, the articulation between the humeral condyles $18_{M,L}$ and ulnar bearings 5a,b is not completely conforming in the sagittal plane ($R_{3h}$<$R_{3u}$) as illustrated in FIG. 33. The ratio of $R_{3h}/R_{3u}$ is approximately 0.95.

Figure 34:
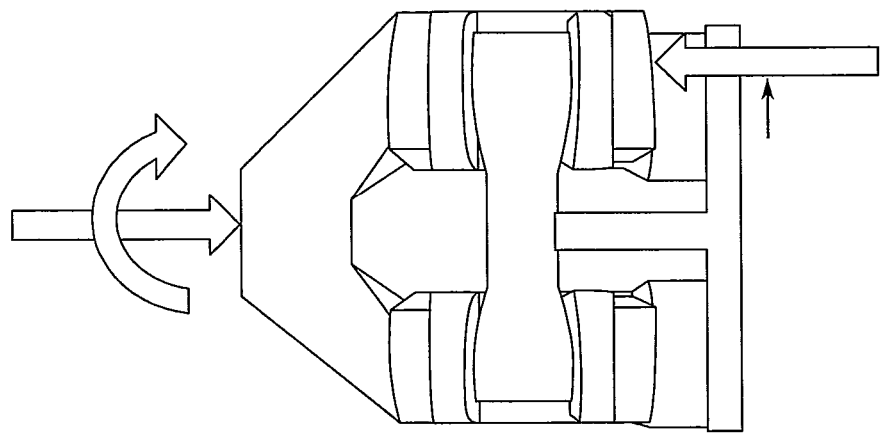
FIG. 34 illustrates a shift in contact point at articulation as external moment is applied in accordance with some embodiments of the disclosed subject matter.
Figure 34:
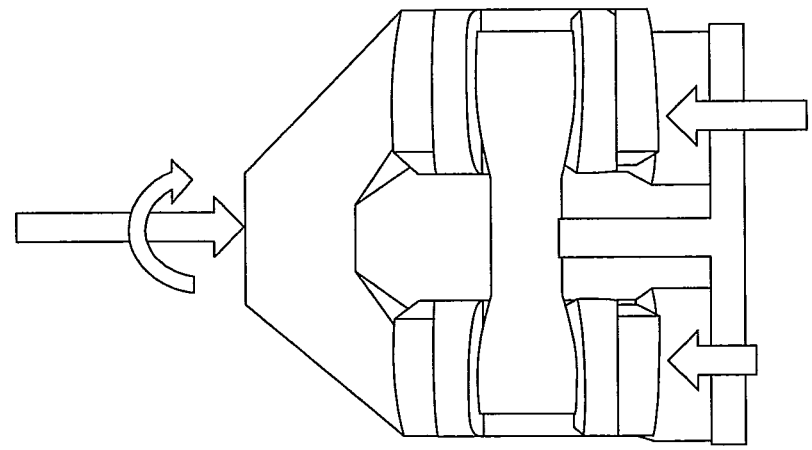
Figure 34:
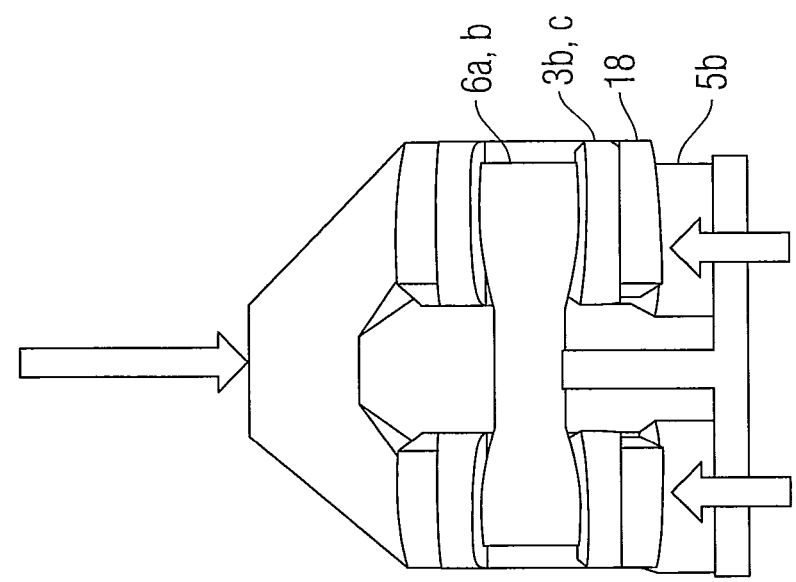
Figure 35A:
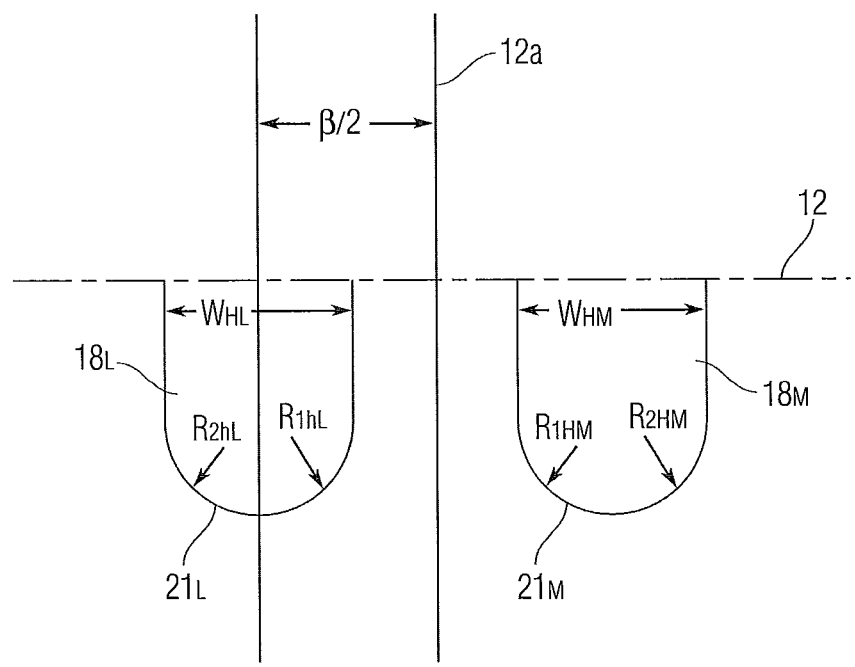
FIG. 35A illustrates differences in articular geometry of the humeral condyles in accordance with some embodiments of the disclosed subject matter.
Figure 35B:
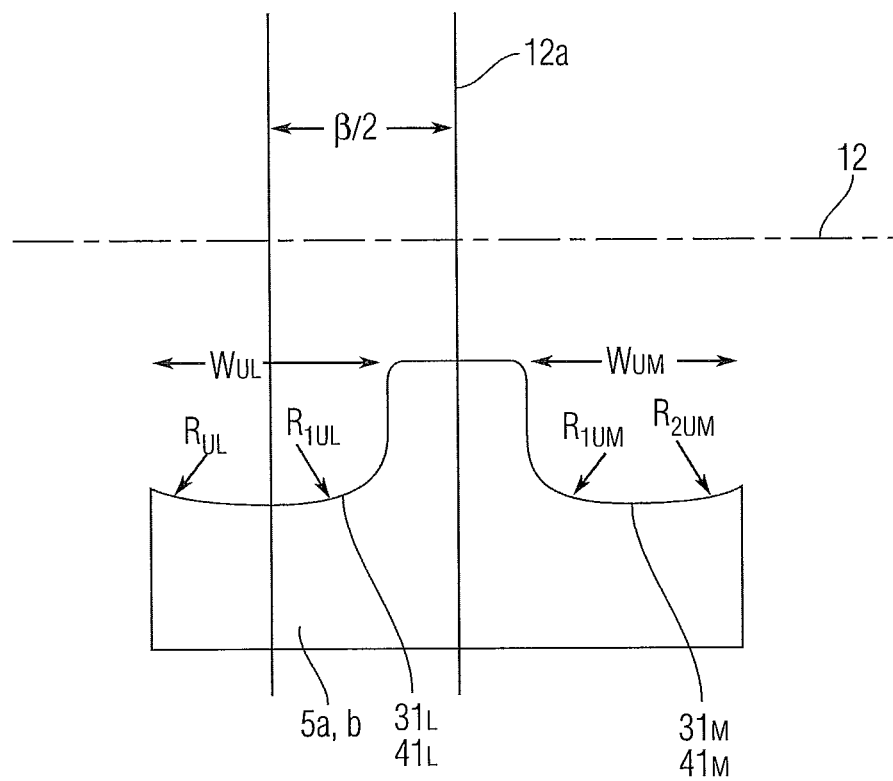
FIG. 35B illustrates differences in articular geometry of the ulnar bearing surfaces in accordance with some embodiments of the disclosed subject matter.
Figure 35C:
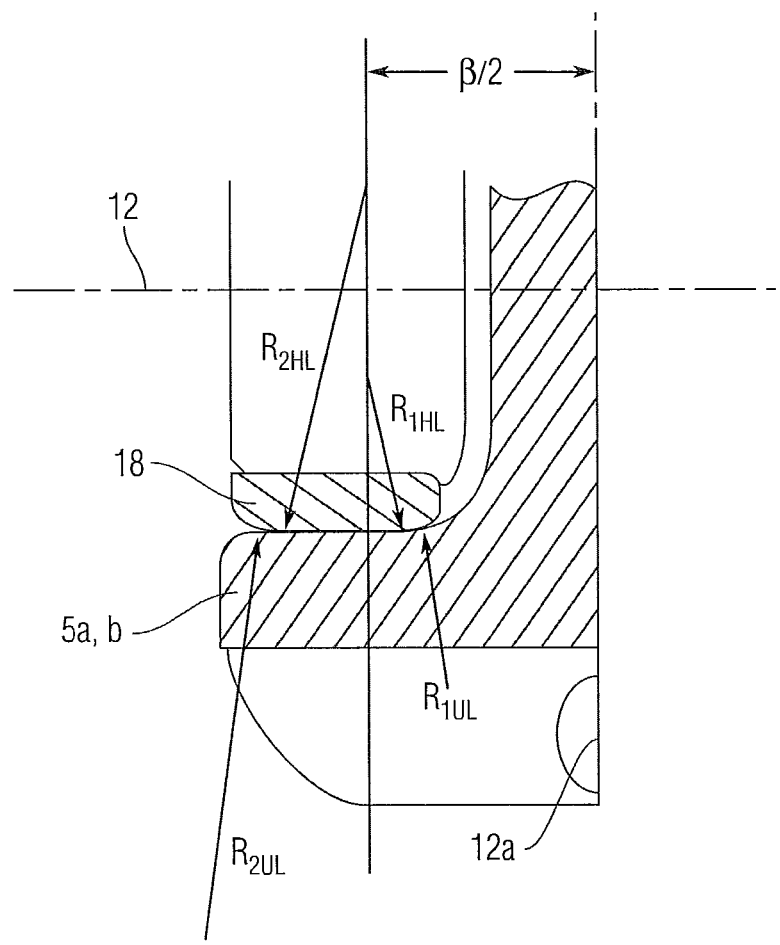
FIG. 35C illustrates the articulation between the humeral and ulnar components in accordance with some embodiments of the disclosed subject matter.

The articulation between the humeral condyles $18_{M,L}$ and ulnar bearings 5a,b in the coronal plane is also not completely conforming as seen in FIGS. 34 and 35C. The humeral condylar articular surfaces $21_{M,L}$ has a principal axis of rotation as defined by joint axis 12 as seen in FIGS. 35A,B,C. FIGS. 35A and 35C show articular surface $21_L$ that has a principal axis (axis 12) but instead is defined by at least two different radii, namely, radii $R_{1HL}$ (near midline 12a) and $R_{2HL}$ (away from midline 12a) that tangentially meet at a distance β/2 away from midline 12a. Radii $R_{1HL}$ and $R_{2HL}$ are revolved around joint axis 12 to create a convex surface. In other words, the bearing surface (articular surface $21_L$, $21_m$) of each condyle $18_{M,L}$ is defined by at least two different radii.

In the figures, radius $R_{1HL}$ represents an inner (medial) radius of the lateral condyle $18_L$, while radius $R_{2HL}$ represents an outer (lateral) radius of the lateral condyle $18_L$. Similarly, radius $R_{1HM}$ represents an inner (medial) radius of the medial condyle $18_M$, while radius $R_{2HM}$ represents an outer (lateral) radius of the medial condyle $18_M$. It will therefore thus be appreciated that the radii of the condyles $18_{M,L}$ at the center of the implant are different than the radii at the outer edges of the respective condyles (lateral edges of the implant).

The medial-lateral width of condyles $18_M$ and $18_L$ are defined by $W_{HM}$ and $W_{HL}$, respectively. The medial articular surface $21_M$ can be different relative to the lateral articular surface $21_L$ in that the widths of the medial and lateral articular surfaces can be different and also, in particular, the two surfaces can be different from one another when the following conditions exist: radius $R_{1HM}$ not equal to $R_{1HL}$; radius $R_{2HM}$ not equal to $R_{2HL}$, and/or $W_{HM}$ not equal to $W_{HL}$.

The ulnar component has similar design in that the articular surface $31_L,41_L$, as illustrated in FIGS. 35B and 35C, is defined by at least two different radii, namely, radii $R_{1UL}$ (near midline 12a) and $R_{2UL}$ (away from midline 12a) that are revolved around joint axis 12 to create a concave surface. In the figures, radius $R_{1UL}$ represents an inner (medial) radius of the lateral surface $31_L$, $41_L$, while radius $R_{2UL}$ represents an outer (lateral) radius of the lateral surface $31_L$, $41_L$. Similarly, radius $R_{1UM}$ represents an inner (medial) radius of the medial surface $31_M$, $41_M$, while radius $R_{2UM}$ represents an outer (lateral) radius of the medial surface $31_M$, $41_M$. It will therefore thus be appreciated that the radii of the surface $31_{M,L}$ and $41_{M,L}$ at the center of the implant are different than the radii at the outer edges of the respective condyles (lateral edges of the implant).

The medial-lateral width of surfaces $31_M$ and $41_M$ is defined by $W_{UM}$. The medial-lateral width of surfaces $31_L$, $41_L$ is defined by $W_{UL}$. The medial articular surfaces $31_M$ and $41_M$ can be different than the lateral articular surfaces $31_M$ and $41_M$, respectively, when the following conditions exist: radius $R_{1UM}$ not equal to $R_{1UL}$; radius $R_{2UM}$ not equal to $R_{2UL}$, and/or $W_{UM}$ not equal to $W_{UL}$.

As with the CCK design, as the two radii humeral condyle 18 pivots about respective two radii ulnar bearing surface 31,41 with an applied external moment, as seen in FIGS. 34 and 35C, the contact location on respective articulation shifts outwardly (away from midline 12a) thereby gradually increasing the restoring moment.

The articular surfaces $31_{M,L}$ of unlinked ulnar bearing 5a are very similar to articular surfaces $41_{M,L}$. The unlinked bearing 5a can have a raised distal face and extends further superiorly than linked bearing 5b. As a result, the concavity opens up at these extending regions to increase range of motion of the elbow joint.

Accordingly, the articulation between the humeral condyles $18_{M,L}$ and ulnar bearings 5a,b in the coronal plane is not completely conforming as illustrated in FIGS. 34 and 35C. The ratios of $R_{1HL}/R_{1UL}$, $R_{1HM}/R_{1UM}$, $R_{2HL}/R_{2UL}$, and $R_{2HM}/R_{2UM}$ are approximately 0.85-0.98.

It will be understood that the top arrow in FIG. 34 describes an applied compressive force (F) across the joint, and the 2 bottom arrows describe the joint reaction force (F/2). As a varus moment (M+) (represented by the first curved arrow) is applied, the joint reaction force (F+) becomes greater on the medial side (longer bottom arrow) than the lateral side (shorter bottom arrow). As a greater varus moment (M++) (represented by the second curved arrow) is applied, the joint reaction force (F++) is completely on the medial side creating lift-off on the lateral side (i.e., the bearing surface (articular surface) of the lateral condyle lifts off and away from contact with the corresponding bearing surface (articular surface) of the ulnar bearing component). In addition, the contact location of joint reaction force (F++) and shifts outwardly distance X as $R_{2HL}$ rolls onto $R_{2UL}$ as indicated in the rightmost figure of FIG. 34.

Thus, in accordance with one embodiment of the present invention, the bearing surfaces of the humeral condyles $18_{M,L}$ and ulnar bearings 5a,b are not toroidal in shape but instead, each of the associated bearing surfaces has a cross-section in a coronal plane that exhibits at least two different radii. This construction provides for a shifting or migrating contact (in the lateral direction) between the two mating components during movement between the two components and provides for the advantages described herein.

Ankle Implant System

In accordance with another embodiment, the teachings of the present invention can be applied to an ankle prosthesis.

Figure 37:
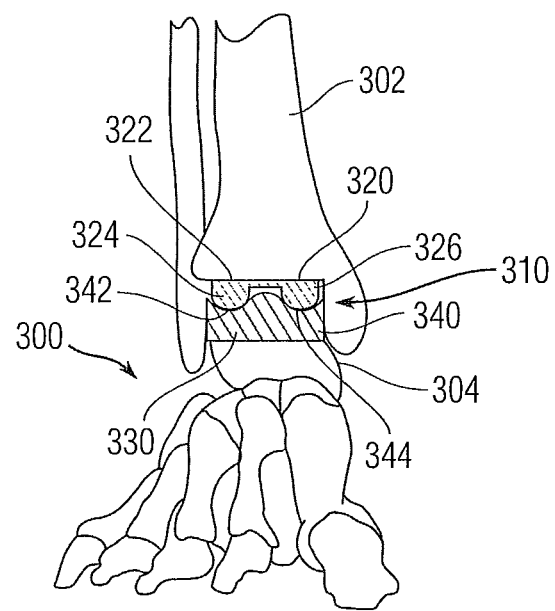
FIG. 37 shows a prosthesis according to the present embodiment for use in ankle joint.

With reference to FIG. 37, an ankle joint 300 is illustrated and is formed where the foot and leg meet. The ankle joint 300 (talocrural joint) is a synovial hinge joint that connects the distal ends of the tibia 302 and fibula in the lower limb with the proximal end of the talus bone 304 in the foot. The articulation between the tibia 302 and the talus 304 bears more weight than between the smaller fibula and the talus 304.

Similar to the previous embodiments described herein, a prosthetic condylar joint 310 can be incorporated between the tibia 302 and talus 304. The prosthetic condylar joint 310 is formed of a first implant component 320 (e.g., a tibial component) and a second implant component 330 (e.g., a talus component) that articulates with the first implant component 320 during normal ankle joint movements.

The first implant component 320 is formed of a body 322 that has a pair of laterally spaced-apart femoral condylar portions 324, 326, each of which is smoothly convexly curved in a lateral profile. The second component 330 cooperates with the first implant component 320 to provide for the desired kinematics of the ankle prosthesis. The second component 330 can include a body 340 that has an upper surface that can be flat or have some other predetermined contour. A pair of laterally spaced-apart, oblong concavities 342, 344 is formed along the upper surface for receiving femoral condylar portions 324,326 of the first implant component 320 as described below. The "nested" support of the first implant component 320 stabilizes the prosthetic joint, but still permits movements that are involved in normal function of the anatomical ankle joint.

It will be understood that both the first and second implant components 320, 330 can be fixedly attached to the respective bones using conventional techniques including stems that are fixedly attached to the implant components and can be fixedly implanted into the bones.

Similar to the other different prosthetic joints described herein, the shape of the first implant component 320 (as well as the second implant component 330) had been modified so that the geometry is no longer a swept circular shape (i.e., a toroid). Instead, the swept geometry consists of two tangent radii, for which the medial radius of each condyle 324, 326 is smaller than the lateral radius thereof.

As mentioned above, the pair of laterally spaced-apart, oblong concavities 342, 344 is formed along the upper surface for receiving condylar portions 324, 326 of the first implant component 320 and therefore, have complementary shapes relative to the condylar portions 324, 326. Accordingly and similar to the first implant component 320, the contact bearing surfaces 342, 344 of the second implant component 330 do not have swept circular shape (i.e., a toroid) but instead, the swept geometry consists of at least two tangent radii (curved articular geometry). Each bearing surface 342, 344 has a first radius (medial) and a second radius (lateral), with the medial radius being less than the lateral radius. This design is complementary to the design of the bearing surfaces of the first implant component 320 and therefore, when the two mate together, the reduced medial radii portions of the component overlie one another and lateral radii portions of the components overlie one another.

As the ankle rotates into varus or valgus, the contact point between the two components 320, 330 shifts away from the center of the ankle. When the ankle undergoes varus/valgus rotation, the contact point between the first and second implant components 320, 330 shifts and more specifically, shifts in a direction away from the center. In other words, the design of the first implant component 320 and the first implant component 330 provide for a migrating (translating) bearing contact point (in the lateral direction) between the first and second implant components 320, 330 as the ankle undergoes varus or valgus rotation.

The present invention thus provides for improved prosthetic condylar joints with articulating bearing surfaces having a translating contact point during rotation thereof.

In each of the embodiments, the construction of the bearing surfaces of the condylar components and the corresponding mating implant components provides a translating contact point (which moves in an outward (lateral) direction away from the center of the joint) with respect to each of the condyles. This translating movement is in contrast to the movement of conventional implants and provides the advantages described herein. This movement results in increased joint stability and provides prosthetic joints that overcome the deficiencies associated with the conventional devices.

While the invention has been described in connection with certain embodiments thereof, the invention is capable of being practiced in other forms and using other materials and structures. Accordingly, the invention is defined by the recitations in the claims appended hereto and equivalents thereof.

What is claimed is:

1. A prosthetic joint comprising:
 a first implant component for attachment to a first bone, the first implant component having a bicondylar portion that includes first and second condylar bearing surfaces, wherein each of the first and second condylar bearing surfaces has a convex shape; and
 a second implant component for attachment to a second bone, the second implant component having bearing surfaces that receive and are complementary to the first and second condylar bearing surfaces;
 wherein each of the first and second condylar bearing surfaces and each of the bearing surfaces of the second implant component has a cross-section in a coronal plane that exhibits at least two different radii and a contact point is established between the first and second condylar bearing surfaces and the bearing surfaces of the second implant component, the at least two different radii of each respective condylar bearing surface defining the convex shape of the respective condylar bearing surface;
 wherein varus and valgus rotation of the first implant component relative to the second implant component causes the contact point to move laterally (outwardly) away from a center of the joint when the second implant component is in near full extension relative to the first implant component.

2. The prosthetic joint of claim 1, wherein the first bone is a femur bone and the second bone is a tibia bone.

3. The prosthetic joint of claim 1, wherein the first bone is a humerus bone and the second bone is an ulna bone.

4. The prosthetic joint of claim 1, wherein the first bone is a tibia bone and the second bone is a talus bone.

5. The prosthetic joint of claim 1, wherein a medial (inner) radius of each of the first and second condylar bearing surfaces is less than a lateral (outer) radius thereof.

6. The prosthetic joint of claim 1, wherein the second implant component includes first and second laterally spaced-apart, oblong concavities formed along an upper surface for receiving the first and second condylar bearing surfaces of the first implant component to provide a nested configuration between the first and second implant components, the oblong concavities defining the bearing surfaces of the second implant component.

7. The prosthetic joint of claim 1, wherein the first implant component comprises a femoral component that includes an intercondylar box and the second implant component includes a tibial insert component that has a constraint post for reception within the intercondylar box.

8. The prosthetic joint of claim 1, wherein the first implant component comprises a humeral implant component and the second implant component comprises an ulnar implant component, wherein one end of the humeral implant component includes the bicondylar portion that mates with the bearing surfaces that are formed as part of the ulnar implant component.

9. A prosthetic joint comprising:
 a first implant component for attachment to a first bone, the first implant component having a bicondylar portion that includes first and second condyles that are spaced apart and define first and second condylar bearing surfaces, respectively, wherein each of the first and second condylar bearing surfaces has a convex shape; and
 a second implant component for attachment to a second bone, the second implant component having concave shaped bearing surfaces that receive and are complementary to the first and second condylar bearing surfaces;

wherein each of the first and second condylar bearing surfaces and each of the bearing surfaces of the second implant component has a cross-section in a coronal plane that exhibits two different radii and a contact point is established between the first and second condylar bearing surfaces and the bearing surfaces of the second implant component, the at least two different radii of each respective condylar bearing surface defining the convex shape of the respective condylar bearing surface;

wherein during a prescribed movement between the first and second implant components, the contact point moves outwardly away from a center of the joint when the second implant component is in near full extension relative to the first implant component.

10. The prosthetic joint of claim 9, wherein the prescribed movement comprises a varus or valgus motion.

11. The prosthetic joint of claim 10, wherein the prosthetic joint is selected from the group consisting of: a prosthetic knee joint, a prosthetic elbow joint, and a prosthetic ankle joint.

* * * * *